United States Patent
Audia et al.

(10) Patent No.: US 7,468,365 B2
(45) Date of Patent: Dec. 23, 2008

(54) LACTAM COMPOUND

(75) Inventors: James Edmund Audia, Zionsville, IN (US); Benjamin Alan Diseroad, Martinsville, IN (US); Varghese John, San Francisco, CA (US); Lee H. Latimer, Oakland, CA (US); Jeffrey Scott Nissen, Indianapolis, IN (US); Gregory Alan Stephenson, Fishers, IN (US); Eugene D. Thorsett, Half Moon Bay, CA (US); Jay S. Tung, Belmont, CA (US)

(73) Assignees: Eli Lilly and Company, Indianapolis, IN (US); Elan, South San Francisco, CA (US)

( * ) Notice: Subject to any disclaimer, the term of this patent is extended or adjusted under 35 U.S.C. 154(b) by 283 days.

(21) Appl. No.: 11/329,859

(22) Filed: Jan. 11, 2006

(65) Prior Publication Data

US 2007/0299053 A1  Dec. 27, 2007

Related U.S. Application Data

(63) Continuation-in-part of application No. 10/416,771, filed as application No. PCT/US01/27799 on Nov. 5, 2001, now abandoned, application No. 11/329,859, which is a continuation-in-part of application No. 10/415,057, filed as application No. PCT/US01/27796 on Nov. 2, 2001, now abandoned, application No. 11/329,859, which is a continuation-in-part of application No. 10/415,548, filed as application No. PCT/US01/27795 on Nov. 2, 2001, now abandoned.

(60) Provisional application No. 60/249,552, filed on Nov. 17, 2000, provisional application No. 60/249,655, filed on Nov. 17, 2000, provisional application No. 60/249,656, filed on Nov. 17, 2000.

(51) Int. Cl.
   *C07D 223/16* (2006.01)
   *A61K 31/55* (2006.01)
   *A61P 25/28* (2006.01)

(52) U.S. Cl. .................. 514/212.07; 540/523
(58) Field of Classification Search ................ 540/523; 514/212.07
   See application file for complete search history.

(56) References Cited

U.S. PATENT DOCUMENTS

| 5,283,241 | A | 2/1994 | Bochis et al. |
| 5,284,841 | A | 2/1994 | Chu et al. |
| 5,596,000 | A | 1/1997 | Esser et al. |
| 6,635,632 | B1 | 10/2003 | Wu et al. |
| 7,153,847 | B2 | 12/2006 | Wu et al. |

FOREIGN PATENT DOCUMENTS

| WO | WO 98/28268 | | 7/1998 |
| WO | WO 02/40421 | A2 | 5/2002 |
| WO | WO 02/40508 | A2 | 5/2002 |
| WO | WO 02/47671 | A2 | 6/2002 |

OTHER PUBLICATIONS

Reiffen, Manred et al., Specific Bradycardic Agents. 1. Chemistry, Pharmacology, and Structure-Activity Relationships of Substituted Benzazepinones, a New Class of Compounds Exerting Antiischemic Properties, J. Med. Chem., 1990, 1496-1504, 33(5).

Devita, Roberg J. et al., Heterocyclic analogs of the Benzolactam Nucleus of the Non-Peptidic Growth Hormone Secretagogue L-692,429, Bioorganic & Medicinal Chemistry Letters, 1995, 1281-1286, 5(12).

*Primary Examiner*—Bruck Kifle
(74) *Attorney, Agent, or Firm*—Robert D. Titus

(57) ABSTRACT

The present invention provides crystalline (N)-((S)-2-hydroxy-3-methyl-butyryl)-1-(L-alaninyl)-(S)-1-amino-3-methyl-2,3,4,5-tetrahydro-1H-3-benzazepin-2-one, a crystalline anydrate and dihydrates thereof, compositions comprising (N)-((S)-2-hydroxy-3-methyl-butyryl)-1-(L-alaninyl)-(S)-1-amino-3-methyl-2,3,4,5-tetrahydro-1H-3-benzazepin-2-one, its crystalline anhydrate or dihydrate, and methods for using the same.

15 Claims, No Drawings

LACTAM COMPOUND

CROSS-REFERENCE

This application is a continuation-in-part of application Ser. No. 10/416,771 filed Oct. 30, 2003, now abandoned which is a 371 of PCT/US01/27799 filed Nov. 5, 2001 which claims benefit of 60/249,552 filed Nov. 17, 2000; Ser. No. 10/415,057 filed Sep. 3, 2003, now abandoned which is a 371 of PCT/US01/27796 filed Nov. 2, 2001 which claims benefit of 60/249,655 filed Nov. 17, 2000; and Ser. No. 10/415,548 filed Apr. 28, 2003, now abandoned which is a 371 of PCT/US01/27795 filed Nov. 2, 2001 which claims benefit of 60/249,656 filed Nov. 17, 2000.

FIELD OF THE INVENTION

The present invention relates to the field of pharmaceutical and organic chemistry and is concerned with a compound which inhibits β-amyloid peptide release and/or its synthesis.

BACKGROUND OF THE INVENTION

Certain lactams, which inhibit β-amyloid peptide release and/or its synthesis, and accordingly, are useful for treating Alzheimer's disease, are described in PCT Application No. PCT/US97/22986.

The present invention provides (N)-((S)-2-hydroxy-3-methyl-butyryl)-1-(L-alaninyl)-(S)-1-amino-3-methyl-2,3,4,5-tetrahydro-1H-3-benzazepin-2-one and the dihydrate thereof, which are useful for inhibiting β-amyloid peptide release and/or its synthesis, and, accordingly, are useful in treating Alzheimer's disease and have advantageous efficacy and safety properties.

Since (N)-((S)-2-hydroxy-3-methyl-butyryl)-1-(L-alaninyl)-(S)-1-amino-3-methyl-2,3,4,5-tetrahydro-1H-3-benzazepin-2-one and the dihydrate thereof are useful for treating Alzheimer's disease, there is a need to produce them as pure, stable, and crystalline forms in order to fulfill exacting pharmaceutical requirements and specifications. In addition, the product should be in a form that is readily filtered, easily dried, and conveniently stored. The novel crystalline anhydrate and dihydrate forms of this invention have suitable properties to be conveniently formulated on a commercial scale in, for example, tablets for oral administration, and have suitable processing and storage properties.

SUMMARY OF THE INVENTION

This invention provides (N)-((S)-2-hydroxy-3-methyl-butyryl)-1-(L-alaninyl)-(S)-1-amino-3-methyl-2,3,4,5-tetrahydro-1H-3-benzazepin-2-one.

In another embodiment, the present invention provides a pharmaceutical composition comprising (N)-((S)-2-hydroxy-3-methyl-butyryl)-1-(L-alaninyl)-(S)-1-amino-3-methyl-2,3,4,5-tetrahydro-1H-3-benzazepin-2-one and a pharmaceutically acceptable diluent.

In a further embodiment, the present invention provides (N)-((S)-2-hydroxy-3-methyl-butyryl)-1-(L-alaninyl)-(S)-1-amino-3-methyl-2,3,4,5-tetrahydro-1H-3-benzazepin-2-one anhydrate.

In another embodiment, the present invention provides a pharmaceutical composition comprising (N)-((S)-2-hydroxy-3-methyl-butyryl)-1-(L-alaninyl)-(S)-1-amino-3-methyl-2,3,4,5-tetrahydro-1H-3-benzazepin-2-one anhydrate and a pharmaceutically acceptable diluent.

This invention also provides crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α.

In another embodiment, the present invention provides a pharmaceutical composition comprising crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α and a pharmaceutically acceptable diluent.

This invention also provides crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β.

In another embodiment, the present invention provides a pharmaceutical composition comprising crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β and a pharmaceutically acceptable diluent.

This invention further provides (N)-((S)-2-hydroxy-3-methyl-butyryl)-1-(L-alaninyl)-(S)-1-amino-3-methyl-2,3,4,5-tetrahydro-1H-3-benzazepin-2-one dihydrate.

In another embodiment, the present invention provides a pharmaceutical composition comprising (N)-((S)-2-hydroxy-3-methyl-butyryl)-1-(L-alaninyl)-(S)-1-amino-3-methyl-2,3,4,5-tetrahydro-1H-3-benzazepin-2-one dihydrate and a pharmaceutically acceptable diluent.

This invention also provides crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate.

In another embodiment, the present invention provides a pharmaceutical composition comprising crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate and a pharmaceutically acceptable diluent.

In one of its method aspects, this invention is directed to a method for inhibiting β-amyloid peptide release and/or its synthesis comprising administering to a patient in need thereof an effective amount of (N)-((S)-2-hydroxy-3-methyl-butyryl)-1-(L-alaninyl)-(S)-1-amino-3-methyl-2,3,4,5-tetrahydro-1H-3-benzazepin-2-one, (N)-((S)-2-hydroxy-3-methyl-butyryl)-1-(L-alaninyl)-(S)-1-amino-3-methyl-2,3,4,5-tetrahydro-1H-3-benzazepin-2-one anhydrate, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β, (N)-((S)-2-hydroxy-3-methyl-butyryl)-1-(L-alaninyl)-(S)-1-amino-3-methyl-2,3,4,5-tetrahydro-1H-3-benzazepin-2-one dihydrate, or crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate.

In a particular method embodiment, the present invention provides a method for treating Alzheimer's disease comprising administering to a patient in need thereof an effective amount of (N)-((S)-2-hydroxy-3-methyl-butyryl)-1-(L-alaninyl)-(S)-1-amino-3-methyl-2,3,4,5-tetrahydro-1H-3-benzazepin-2-one, (N)-((S)-2-hydroxy-3-methyl-butyryl)-1-(L-alaninyl)-(S)-1-amino-3-methyl-2,3,4,5-tetrahydro-1H-3-benzazepin-2-one anhydrate, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-e, (N)-((S)-2-hydroxy-3-methyl-butyryl)-1-(L-alaninyl)-(S)-1-amino-3-methyl-2,3,4,5-tetrahydro-1H-3-benzazepin-2-one dihydrate, or crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate.

The present invention also provides a method for preventing or inhibiting the progression of Alzheimer's disease comprising administering to a patient in need thereof with an effective amount of (N)-((S)-2-hydroxy-3-methyl-butyryl)-1-(L-alaninyl)-(S)-1-amino-3-methyl-2,3,4,5-tetrahydro-1H-3-benzazepin-2-one, (N)-((S)-2-hydroxy-3-methyl-butyryl)-1-(L-alaninyl)-(S)-1-amino-3-methyl-2,3,4,5-tetrahydro-1H-3-benzazepin-2-one anhydrate, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β, (N)-((S)-2-hydroxy-3-methyl-butyryl)-1-(L-alaninyl)-(S)-1-amino-3-methyl-2,3,4,5-tetrahydro-1H-3-benzazepin-2-one dihydrate, or crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate.

DETAILED DESCRIPTION OF THE INVENTION

As used herein, the terms below have the meanings indicated:

The term "ee" or "enantiomeric excess" refers to the percent by which one enantiomer, $E_1$, is in excess in a mixture of both enantiomers ($E_1+E_2$), as calculated by the equation (($E_1-E_2$)÷($E_1+E_2$))×100%=ee. As is well known in the art, enantiomeric excess can be determined by capillary electrophoresis and by chiral HPLC of the compounds or derivatives thereof.

Herein, the Cahn-Prelog-Ingold designations of (R)- and (S)- and the designations of L- and D- for stereochemistry relative to the isomers of glyceraldehyde are used to refer to specific isomers.

The present invention provides (N)-((S)-2-hydroxy-3-methyl-butyryl)-1-(L-alaninyl)-(S)-1-amino-3-methyl-2,3,4,5-tetrahydro-1H-3-benzazepin-2-one, and in particular, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β, and a crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate. The skilled artisan will appreciate that alternate naming conventions may be applied to this structure resulting in multiple names for the same species. For example, the Chemical Abstracts Index name is Butanamide, 2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl-, (2S)-. Another name for the compound of the invention is (2S)-N-{(1S)-1-[N-(1S)-3-methyl-2-oxo-(1H, 4H, 5H-benzo[d]azaperhydroepinyl)-carbamoyl]ethyl}-2-hydroxy-3-methylbutanamide. All these names are synonyms for (N)-((S)-2-hydroxy-3-methyl-butyryl)-1-(L-alaninyl)-(S)-1-amino-3-methyl-2,3,4,5-tetrahydro-1H-3-benzazepin-2-one of the present invention, and may be applied to the anhydrate, dihydrate and various crystal forms described herein as well.

The compound (N)-((S)-2-hydroxy-3-methyl-butyryl)-1-(L-alaninyl)-(S)-1-amino-3-methyl-2,3,4,5-tetrahydro-1H-3-benzazepin-2-one can be prepared as described below. In the Schemes below, all substituents, unless otherwise indicated, are as previously defined and all reagents are well known and appreciated in the art.

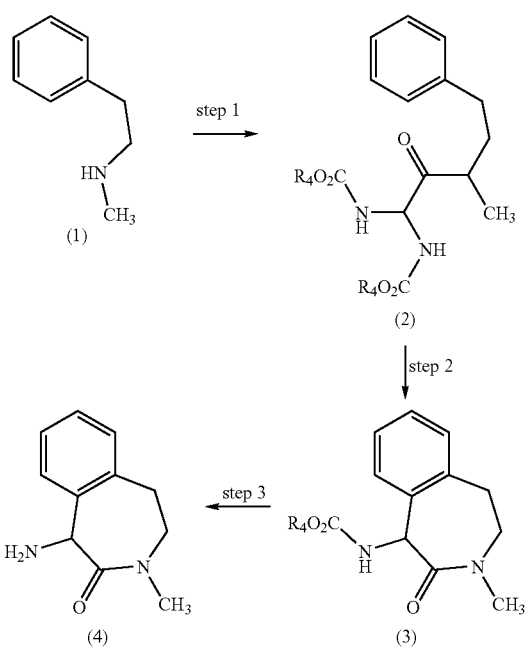

Scheme 1

In Scheme 1, step 1, N-methylphenethylamine of formula (1) is acylated with a suitable bisalkoxycarbonylacetate transfer reagent to give a compound of formula (2). N-methylphenethylamine is commercially available and is readily prepared by the reaction of a 2-bromo or 2-chloroethylbenzene, under conditions well known and appreciated in the art, with an methylamine. A suitable bisalkoxycarbonylacetate transfer reagent is one in which $R_4$ is $C_1$-$C_4$ alkyl and transfers a bisalkoxycarbonylacetyl group to the compound of formula (1), such as, bisalkoxycarbonylacetic acids and bisalkoxycarbonylacetyl chlorides. (See Ben-Ishai, *Tetrahedron*, 43, 439-450 (1987)).

For example, the compound of formula (1) is contacted with a suitable bisalkoxycarbonylacetic acid to give a compound of formula (2). Such coupling reactions are common in peptide synthesis and synthetic methods used therein can be employed. For example, well known coupling reagents such as carbodiimides with or without the use of well known additives such as N-hydroxysuccinimide, 1-hydroxybenzotriazole, etc. can be used to facilitate this acylation. Such coupling reactions often use a suitable base to scavenge the acid generated during the reaction. Suitable bases include, by way of example, triethylamine, N,N-diisopropylethylamine, N-methylmorpholine and the like. The reaction is conventionally conducted in an inert aprotic polar diluent such as dimethylformamide, methylene chloride, chloroform, acetonitrile, tetrahydrofuran and the like. Typically the reaction is carried out at temperatures of from about 0° C. to about 60° C. and typically require from about 1 to about 24 hours. Upon reaction completion, the product of formula (2) is recovered by conventional methods including extraction, precipitation, chromatography, filtration, trituration, crystallization and the like.

Alternatively, for example, the compound of formula (1) is contacted with a suitable bisalkoxycarbonylacetyl chloride to give a compound of formula (2). Such acid chlorides are readily prepared from the corresponding acids by methods well known in the art, such as by the action of phosphorous trichloride, phosphorous oxychloride, phosphorous pentachloride, thionyl chloride, or oxalyl chloride, with or without a small amount of dimethylformamide, in an inert solvent such as, toluene, methylene chloride, or chloroform; at temperatures of from about 0-80° C. The reaction is typically carried out for a period of time ranging from 1 hour to 24 hours. The acid chloride can be isolated and purified or can often be used directly, that is, with or without isolation and/or purification. Such acylation reactions generally use a suitable base to scavenge the acid generated during the reaction. Suitable bases include, by way of example, pyridine, triethylamine, N,N-diisopropylethylamine, N-methylmorpholine and the like. The reaction is conventionally conducted in an inert aprotic polar diluent such as methylene chloride, chloroform, tetrahydrofuran and the like. Typically the reaction is carried out at temperatures of from about –20° C. to about 80° C. and typically require from about 1 to about 24 hours. Upon reaction completion, the product of formula (2) is recovered by conventional methods including extraction, precipitation, chromatography, filtration, trituration, crystallization and the like.

In Scheme 1, step 2, a compound of formula (2) is cyclized to give a compound of formula (3). For example, a compound of formula (2) is contacted with an acid, such as methanesulfonic acid or sulfuric acid. The reaction is typically carried out using the selected acid as a solvent. Typically the reactants are initially mixed at temperatures of from about –20° C. to about 0° C. and then allowed to warm to temperatures of about ambient temperature to about 60° C. The cyclization reaction typically requires from about 12 to about 72 hours. Upon reaction completion, the product of formula (2) is recovered by conventional methods including extraction, precipitation, chromatography, filtration, trituration, crystallization and the like.

In Scheme 1, step 3, a compound of formula (3) is deprotected to give a compound of formula (4). The removal of such alkoxycarbonyl amine protecting groups is well known and appreciated in the art. For example see, *Protecting Groups in Organic Synthesis*, Theodora Greene (1$^{st}$ and 2$^{nd}$ Editions, Wiley-Interscience) and Ben-Ishai, *Tetrahedron*, 43, 439-450 (1987).

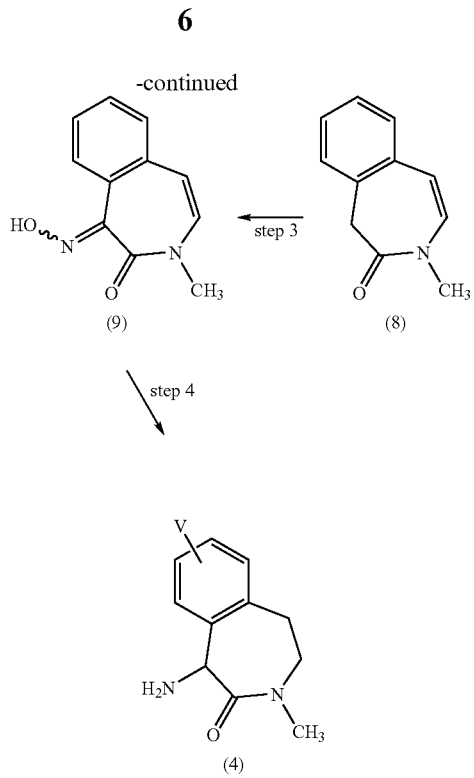

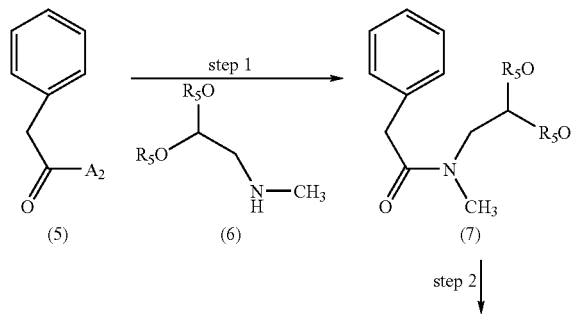

In Scheme 2, step 1, an appropriate phenyl acetic acid of formula (5) is coupled with an appropriate acetal of formula (6) to give a compound of formula (7). An appropriate phenyl acetic acid of formula (5) is one in which $A_2$ is an activated group, for example, —OH, —Cl, or —Br. An appropriate acetal of formula (6) is one in which $R_5$ is a $C_1$-$C_4$ alkyl. Such coupling reactions are common in peptide synthesis and synthetic methods used therein can be employed as are described in Scheme 1, step 1.

Also, the coupling depicted in Scheme 2, step 2, can be carried out under Schotten-Baumann conditions using an acid halide of the compound of formula (5) and an appropriate acetal of formula (6) in a mixed solvent, such as, methyl t-butyl ether, ethyl acetate, tetrahydrofuran, acetone, or diethyl ether and water. Such reactions are carried out using a suitable base, such as sodium hydroxide, potassium hydroxide, sodium carbonate, potassium carbonate, sodium bicarbonate, or potassium bicarbonate. Typically the reaction is stirred or agitated vigorously and is carried out at temperatures of from about –20° C. to about 80° C. and typically require from about 1 to about 24 hours. Upon reaction completion, the product of formula (7) is recovered by conventional methods including extraction, precipitation, chromatography, filtration, trituration, crystallization and the like.

In Scheme 2, step 2, a compound of formula (7) is cyclized to give a compound of formula (8). Such cyclization reactions are carried out in an acid, such as sulfuric acid. Typically the acid is used as the solvent. In general, the reaction is carried out at temperatures of from about –20° C. to about 150° C. and typically require from about 1 to about 24 hours. Upon reaction completion, the product of formula (8) is recovered by conventional methods including extraction, precipitation, chromatography, filtration, trituration, crystallization and the like.

In Scheme 2, step 3, a compound of formula (8) undergoes an amine transfer reaction to give a compound of formula (9). In Scheme 2 an oximation is depicted. Such oximations are accomplished by contacting the enolate of a compound of formula (8) with an oxime transfer reagent, such as an alkyl nitrite ester. The enolate of a compound of formula (8) can be prepared by reacting the compound of formula (8) with a suitable base, such as potassium t-butoxide, lithium diisopropylamide, lithium hexamethylsilazide, sodium hexamethylsilazide, potassium hexamethylsilazide, and the like. Such oximinations are exemplified by Wheeler, et al., Organic Syntheses, Coll. Vol. VI, p. 840 which describes the reaction of isoamyl nitrite with a ketone to prepare the desired oxime.

The reaction is typically carried out in a solvent, such as tetrahydrofuran. In general, the reaction is carried out at temperatures of from about −20° C. to about 50° C. and typically require from about 1 to about 24 hours. Upon reaction completion, the product of formula (8) is recovered by conventional methods including extraction, precipitation, chromatography, filtration, trituration, crystallization and the like.

Alternately, such an amine transfer reaction can be accomplished through the azide. An azide can be formed by the reaction of the enolate of a compound of formula (8) with an azide transfer reagent, such as toluenesulfonyl azide and triisopropylbenzene-sulfonyl azide. Such reaction are exemplified in Evans, et al., J. Am. Chem. Soc., 112:4011-4030 (1990)41. The reaction is typically carried out in a solvent, such as tetrahydrofuran. In general, the reaction is carried out at temperatures of from about—20° C. to about 50° C. and typically require from about 1 to about 24 hours. Upon reaction completion, the product of formula (8) having an azide instead of an oxime is recovered by conventional methods including extraction, precipitation, chromatography, filtration, trituration, crystallization and the like.

As depicted in Scheme 2, step 4, an oxime is reduced to the compound of formula (4). Such reductions are accomplished by treatment with hydrogen and a suitable catalyst, such as Raney-nickel or palladium catalysts, such as palladium-on-carbon. The reaction is typically carried out in a solvent, such as tetrahydrofuran, ethyl acetate, or lower alcohols, such as methanol, ethanol, and isopropanol, in acetic acid, water, aqueous ammonia, and the like, and mixtures thereof. The reaction generally carried out at hydrogen pressures ranging from atmospheric pressure to about 600 psi. (4137 kPa). In general, the reaction is carried out at temperatures of from about 20° C. to about 100° C. and typically require from about 1 to about 24 hours. Upon reaction completion, the product of formula (4) is recovered by conventional methods including extraction, precipitation, chromatography, filtration, crystallization and the like.

Alternately, where the amine is transferred via an azide, the azido group is reduced. Such reductions are carried out by hydrogenation as described above.

Processes for making (N)-((S)-2-hydroxy-3-methyl-butyryl)-1-(L-alaninyl)-(S)-1-amino-3-methyl-2,3,4,5-tetrahydro-1H-3-benzazepin-2-one are described in Scheme A.

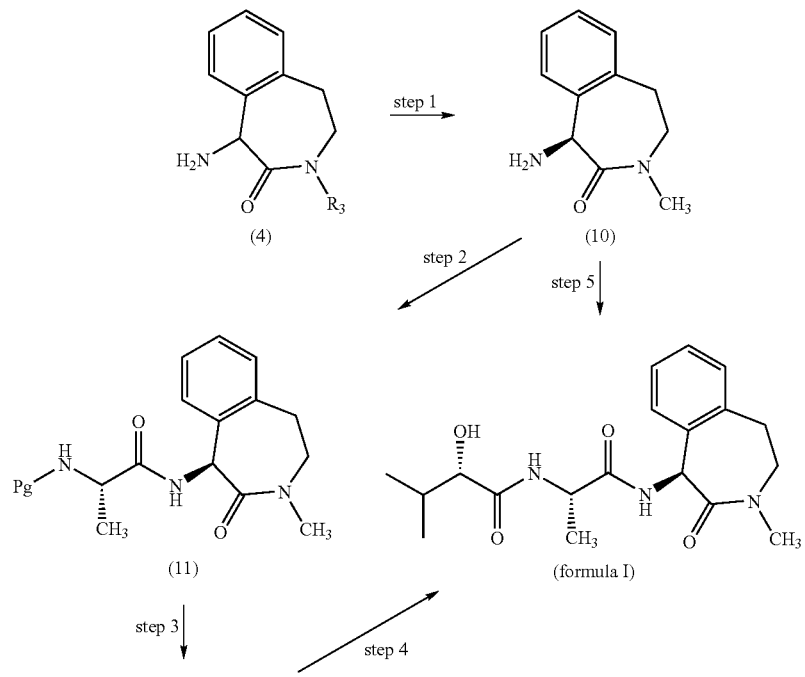

Scheme A

-continued

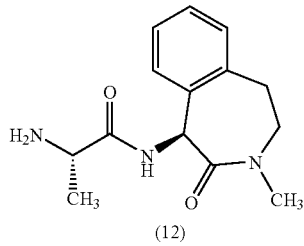

(12)

Scheme A, step 1, depicts the stereochemical resolution of an appropriate lactam of formula (4) to give a lactam, of formula (10), that is, of a substantially pure (S)-1-amino-3-methyl-2,3,4,5-tetrahydro-1H-3-benzazepin-2-one. As used herein the term "substantially pure" refers to enantiomeric purity of (S)-1-amino-3-methyl-2,3,4,5-tetrahydro-1H-3-benzazepin-2-one. Accordingly to the present invention substantially pure (S)-1-amino-3-methyl-2,3,4,5-tetrahydro-1H-3-benzazepin-2-one can be prepared comprising the (S)-enantiomer which is greater than 80%, preferably greater than 90%, more preferably greater than 95%, most preferably greater than 97%.

For example, the (S)-isomer of the compound of formula (4) can be resolved by fractional crystallization of dibenzoyl-tartrate, (R)-(−)-d-camphorsulfonic acid, and (D)-(−)-mandelic acid salts. It is expected that a wide variety of dibenzolytartarates are suitable for this purpose. In particular, the dibenzoyl esters having a para substituent selected from the group consisting of hydrogen, halogen, $C_1$-$C_4$ alkyl, and $C_1$-$C_4$ alkoxy are preferred with di-p-toluoyl-tartrate being preferred. Di-p-toluoyl-L-tartrate is used to obtain the (S)-isomer.

According to the present process, the compound of formula (4) is contacted with the selected acid. Generally, from about 0.4 molar equivalents to a large excess of the selected acid can be used with about 0.4 to 1.5 molar equivalents being preferred and with about 0.5 to 1.1 molar equivalents being more preferred.

The process is typically carried out by crystallizing the acid addition salt from a solution. In particular, solvents such as lower alcohols, including methanol, ethanol, n-propanol, iso-propanol, butanol, sec-butanol, iso-butanol, t-butanol, amyl alcohol, iso-amyl alcohol, t-amyl alcohol, hexanol, cyclopentanol, and cyclohexanol are suitable, with methanol, ethanol, and isopropanol being preferred. The use of an anti-solvent may be advantageous. As used herein, the term "anti-solvent" refers to a solvent in which the salt is significantly less soluble compared to solvent. Preferably, when an anti-solvent is used it is miscible with the selected solvent. Suitable anti-solvents include ethers, such as diethyl ether, methyl t-butyl ether, and the like, and lower alkyl acetates, such as methyl acetate, ethyl acetate, iso-propyl acetate, propyl acetate, iso-butyl acetate, sec-butyl acetate, butyl acetate, amyl acetate, iso-amyl acetate, and the like, and alkanes, such as pentane, hexane, heptane, cyclohexane, and the like. When the present process is carried out by crystallizing the acid addition salt from the racemic mixture, care must be taken in using an anti-solvent to avoid crystallization of the salt of the undesired diastereomeric salt.

Typically, the crystallization is carried out at initial temperatures of about 40° C. to reflux temperature of the selected solvent(s) and at initial concentrations of from about 0.05 molar to about 0.25 molar. The mixture is then cooled to give the salt. Seeding may be advantageous. Stirring of the initial precipitate for from about 4 to 48 hours may be advantageous. Preferably the crystallization solution is cooled slowly. The crystallization is most conveniently cooled to temperatures of ambient temperature to about −20° C. The salt can be collected using techniques that are well known in the art, including filtration, decanting, centrifuging, evaporation, drying, and the like. The compound of formula (10) can be used directly as the acid addition salt of the selected acid. Alternately, before use the compound of formula (10) can be isolated as another acid addition salt after acid exchange or can by isolated as the base by extraction under basic conditions as is well known and appreciated in the art.

A preferred process gives (S)-1-amino-3-methyl-2,3,4,5-tetrahydro-1H-3-benzazepin-2-one of substantial enantiomeric purity by crystallizing 1-amino-3-methyl-2,3,4,5-tetrahydro-1H-3-benzazepin-2-one as its acid addition salt of an acid selected from the group consisting of di-p-tolyl-L-tartaric acid, (R)-(−)-d-camphorsulfonic acid, and (D)-(−)-mandelic acid as a dynamic process in the presence of an aromatic aldehyde. The dynamic process has the advantage that the 1-amino-3-methyl-2,3,4,5-tetrahydro-1H-3-benzazepin-2-one undergoes conversion to a single isomer during the crystallization, thus, improving the yield and avoiding a waste stream which includes an undesired isomer.

It is expected that a wide variety of aromatic aldehydes are suitable for the dynamic process, we have found that a number of aldehydes are particularly suitable in practice. Specifically, we have found that salicylic acids are preferred and salicylaldehyde, 5-nitrosalicylaldehyde, and 3,5-dichlorosalicylaldehyde are more preferable in the present dynamic resolution process.

Accordingly, when the present process is carried out as a dynamic resolution, 1-amino-3-methyl-2,3,4,5-tetrahydro-1H-3-benzazepin-2-one is contacted with the selected acid in the presence of an aromatic aldehyde. Generally, for the dynamic resolution from about 0.9 to 1.2 molar equivalents of acid are used, with about 1 molar equivalents being preferred. The aromatic aldehyde is generally used in a catalytic amount. Typically, about 0.5 to 0.001 molar equivalents of aromatic aldehyde are used, with about 0.1 to about 0.01 molar equivalents being preferred.

The dynamic process is typically carried out in a solvent without an anti-solvent as described above. The mixture of 1-amino-3-methyl-2,3,4,5-tetrahydro-1H-3-benzazepin-2-one, the selected acid, and aromatic aldehyde are stirred to allow conversion to the desired isomer. Generally this conversion is carried out at temperatures of from ambient temperature to the refluxing temperature of the solvent. Generally conversion requires 6 to 48 hours.

As will be appreciated by the skilled artisan, when the present process is carried out as a dynamic resolution, use of the acid addition salt of (S)-1-amino-3-methyl-2,3,4,5-tetrahydro-1H-3-benzazepin-2-one can be complicated by the presence of a small amount of aromatic aldehyde in the isolated product. Thus, after dynamic resolution it is preferred that (S)-1-amino-3-methyl-2,3,4,5-tetrahydro-1H-3-benzazepin-2-one be isolated by salt exchange, preferably as the hydrochloride salt, before its use or formation of base.

Scheme A, step 2, depicts the coupling reaction of an appropriate amino-protected alanine of formula the PgNH—CHCH$_3$—C(O)-A and an appropriate lactam of formula (10). Appropriate amino-protected alanine is ones in which Pg is an amine protecting group, is of the L-configuration, and A is an activating group, for example —OH, —Cl, or a mixed anhydride capable of coupling with the amino group of the compound of formula (10). Such amino-protected alanines are readily available to the person skilled in the art.

The coupling reaction depicted in Reaction Scheme A, step 2, involves a reaction which is conventionally conducted for peptide synthesis and synthetic methods used therein can also be employed. Such methods are described in detail in Scheme 1, step 1. One particular embodiment employs EDC as a coupling reagent in a suitable solvent such as toluene or dichloromethane or mixtures thereof.

Reaction Scheme A, step 3, depicts the deprotection of a compound of formula (11) to give a compound of formula (12). Such deprotections of amino protecting groups are well known and appreciated in the art. One particular embodiment involves the deprotection of a compound of formula (11) where Pg is tert-butoxycarbonyl, with methanesulfonic acid or hydrochloric acid in a suitable solvent, such as dichloromethane in combination with toluene or methyl tert-butyl ether (MTBE), a mixture of acetone and water, or a mixture of acetone, water, and tetrahydrofuran (THF).

Reaction Scheme A, step 4, depicts the coupling reaction of an appropriate compound of formula (13), (CH$_3$)$_2$CH—CHOH—C(O)A$_1$ and a compound of formula (12) to give a compound of formula I. The S-isomer of the compound of formula (13) is commercially available and is well known in the art, including PCT Application No. PCT/US97/22986, filed 22 Dec. 1997. The coupling reaction depicted in step 4 is carried out using the acid of formula (13) (compounds in which A$_1$ is —OH) or the acid halide derived therefrom (compounds in which A$_1$ is —Cl or —Br), in a manner similar to those taught in Scheme 1, step 1.

An alternative method for preparing the compounds of formula I is depicted in Scheme A, step 5, which shows the coupling reaction of an appropriate compound of formula (10) and an appropriate compound of formula (14), (CH$_3$)$_2$CH—CHOH—C(O)—NH—CHCH$_3$—C(O)A$_2$, to directly give a compound or formula I. An appropriate compound of formula (10) is as described in step 2. An appropriate compound of formula (14) is one in which has the stereochemistry as desired in the final product of formula I.

Compounds of formula (14) are readily prepared by coupling carboxy-protected amino acids, H$_2$N—CHCH$_3$—C(O)OPg$_1$, with compounds of formula (13) as described above. Again such coupling reactions are well known in the art and afford a product, which after deprotection, provide a compound of formula (14).

The compound of formula I can be isolated and purified by a number of techniques, including crystallization. Crystallization from a solution and slurrying techniques can be used. In particular, the compound of the present invention can be prepared by crystallization from a variety of anhydrous and aqueous solvents. The specific crystallization conditions employed may be varied according to preference, availability of materials, or the particular hydrate or physical form of the compound of the invention that is desired. Suitable solvents include acetone, butan-2-one, lower alcohols (like methanol, ethanol, and isopropanol), acetic acid, and acetonitrile with and without water and heptane, ethyl acetate, diethyl ether, and methyl t-butyl ether.

In another embodiment this invention provides a process for making (N)-((S)-2-hydroxy-3-methyl-butyryl)-1-(L-alaninyl)-(S)-1-amino-3-methyl-2,3,4,5-tetrahydro-1H-3-benzazepin-2-one dihydrate comprising crystallizing (N)-((S)-2-hydroxy-3-methyl-butyryl)-1-(L-alaninyl)-(S)-1-amino-3-methyl-2,3,4,5-tetrahydro-1H-3-benzazepin-2-one from aqueous solvents under conditions which yield crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate.

The precise conditions under which crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate is formed may be empirically determined and it is only possible to give a number of methods which have been found to be suitable in practice.

Thus, for example, (N)-((S)-2-hydroxy-3-methyl-butyryl)-1-(L-alaninyl)-(S)-1-amino-3-methyl-2,3,4,5-tetrahydro-1H-3-benzazepin-2-one dihydrate may be prepared by crystallization under controlled conditions. Crystallization from a solution and slurrying techniques are contemplated to be within the scope of the present process. In particular, the dihydrate of the present invention can be prepared by crystallization from an aqueous solvent. A suitable solvent is one that is capable of containing sufficient water, at the concentrations used, to form the present dihydrate. Preferred solvents are those that are water miscible, such as acetone, lower alcohols (like methanol, ethanol, and isopropanol), acetic acid, and acetonitrile. In practice, it has been found that aqueous acetone is preferred. For a given aqueous solvent the amount of water used will depend on the relative solubility of (N)-((S)-2-hydroxy-3-methyl-butyryl)-1-(L-alaninyl)-(S)-1-amino-3-methyl-2,3,4,5-tetrahydro-1H-3-benzazepin-2-one in the solvent compared to water and whether a crystallization or slurrying technique is used.

A crystallization is generally carried out by dissolving (N)-((S)-2-hydroxy-3-methyl-butyryl)-1-(L-alaninyl)-(S)-1-amino-3-methyl-2,3,4,5-tetrahydro-1H-3-benzazepin-2-one in an aqueous solvent and then allowing the solution to cool, with or without the addition of more water, to give a solid. Typically, the crystallization is carried out at initial temperatures of about 40° C. to reflux temperature of the selected aqueous solvent. The mixture is then cooled to give the crystalline dihydrate. Seeding may be advantageous. Preferably the crystallization solution is cooled slowly. The crystallization is most conveniently cooled to temperatures of ambient temperature to about −20° C.

The precise conditions under which crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α or Form-β are formed may be empirically determined and it is only possible to give a number of methods which have been found to be suitable in practice. In particular, the crystalline anhydrates of the present invention can be prepared by either slurrying (N)-((S)-2-hydroxy-3-methyl-butyryl)-1-(L-alaninyl)-(S)-1-amino-3-methyl-2,3,4,5-tetrahydro-1H-3-benzazepin-2-one dihydrate in an anhydrous solvent or by crystallizing the desired anhydrate form from a solution of (N)-((S)-2-hydroxy-3-methyl-butyryl)-1-(L-alaninyl)-(S)-1-amino-3-methyl-2,3,4,5-tetrahydro-1H-3-benzazepin-2-one dihydrate in an anhydrous solvent. An anhydrous solvent is one that does not contain sufficient water, at the concentrations used, to form hydrated forms of solid (N)-((S)-2-hydroxy-3-methyl-butyryl)-1-(L-alaninyl)-(S)-1-amino-3-methyl-2,3,4,5-tetrahydro-1H-3-benzazepin-2-one. Preferred solvents are acetone, butan-2-one, 3A ethanol, acetonitrile, ethyl acetate, and tetrahydrofuran.

A number of methods are available to characterize crystalline forms of organic compounds. For example, methods include differential scanning calorimetry, solid state NMR spectrometry, infra-red spectroscopy, and X-ray powder diffraction. Among these X-ray powder diffraction and solid state NMR spectroscopy are very useful for identifying and distinguishing between crystalline forms.

X-ray powder diffraction analyses were performed as follows. Either with or without lightly grinding the sample with an agate mortar and pestle, the sample is loaded into a sample holder for the X-ray powder diffraction measurement. The X-ray powder diffraction patterns were measured using a Siemens D5000 X-ray powder diffractometer equipped with a CuK$_\alpha$ source ($\lambda$=1.54056 Å) operated at 50 kV and 40 mA using divergence slit size of 1 mm, receiving slit of 1 mm, and detector slit of 0.1 mm. Each sample was scanned between 4° and 35° (2θ) with a step size of 0.02° and a maximum scan rate of 3 sec/step. Data is collected using a Kevex solid-state silicon lithium detector. Optimally, a silicon standard is run routinely to check the instrument alignment.

It is well known in the crystallography art that, for any given crystal form, the relative intensities and peak widths of the diffraction peaks may vary due to a number of factors, including the effects of preferred orientation and/or particle size. Where the effects of preferred orientation and/or particle size are present, peak intensities may be altered, but the characteristic peak positions of the polymorph are unchanged. See, e.g., The United States Pharmacopoeia #24, National Formulary #19, pages 1843-1844, 2000.

Grinding was used to minimize intensity variations for the peak intensities of some of the diffractogram disclosed herein. However, if grinding significantly altered the diffractogram or alters the crystalline state of the sample, then the diffractogram of the unground sample should be used. Grinding was done in a small agate mortar and pestle. The mortar was held during the grinding and light pressure was applied to the pestle.

Peak position was obtained in 2θ values and peak intensities for the most prominent features (relative intensities greater than 20%) were measured using a double-derivative peak picking method.

Accordingly, an aspect of the present invention is directed to crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α characterized by the X-ray powder diffraction patterns in Table 1, which lists the 2θ values and relative intensities ($I_o/I_{100}$) greater than 20%, measured for an unground sample and for a sample after 5 minutes of grinding and using the methodology described above with CuK$_\alpha$ radiation:

TABLE 1

| Unground | | 5 min grinding | |
|---|---|---|---|
| 2θ (°) | $I_o/I_{100}$(%) | 2θ (°) | $I_o/I_{100}$(%) |
| 4.53 | 100 | 4.486 | 95.5 |
| 5.361 | 25.6 | 5.338 | 31.6 |
| | | 7.313 | 20.1 |
| 9.037 | 20.1 | 8.99 | 25.8 |
| 9.515 | 85 | 9.477 | 100 |
| 9.786 | 46.5 | 9.746 | 86 |

TABLE 1-continued

| Unground | | 5 min grinding | |
|---|---|---|---|
| 2θ (°) | $I_o/I_{100}$(%) | 2θ (°) | $I_o/I_{100}$(%) |
| 11.693 | 24 | 11.649 | 23.3 |
| 12.456 | 31.2 | 12.408 | 47.1 |
| 13.912 | 24.4 | 13.862 | 25.4 |
| 14.716 | 40.5 | 14.667 | 66.7 |
| 16.211 | 21.5 | 16.174 | 30.2 |
| 17.917 | 19.8 | 17.884 | 33.6 |
| | | 18.278 | 42.2 |
| | | 18.79 | 33.3 |
| 19.097 | 22.7 | 19.06 | 35.9 |
| | | 19.359 | 30.9 |
| | | 20.028 | 30.2 |
| | | 23.267 | 24.3 |

The intensities of the sample ground for 5 minutes are more representative of the diffraction pattern where attempts were made to minimize the effects of preferred orientation and/or particle size. It should also be noted that the computer-generated, unrounded numbers are listed in this table.

Thus, a properly prepared sample crystalline of (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α may be characterized by X-ray diffraction pattern in 2θ values using CuK$_\alpha$ radiation having peaks as described in Table 1, and in particular having a peak at 4.53, 5.36, 9.04, 9.52, 9.79, 11.69, 12.46, 13.91, 14.72, 16.21, 17.92, or 19.10; more particularly having a peak at 4.53, 9.52, 9.79, or 14.72; peaks at any two of 4.53, 9.52, 9.79, and 14.72; or at having peaks at 4.53, 5.36, 9.04, 9.52, 9.79, 11.69, 12.46, 13.91, 14.72, 16.21, 17.92, and 19.10.

Crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α may also be characterized by solid state NMR spectroscopy. Solid state $^{13}$C chemical shifts reflect not only the molecular structure of but also the electronic environment of the molecule in the crystal.

Solid state NMR ($^{13}$C) analysis can be carried out using $^{13}$C Cross polarization/magic angle spinning (CP/MAS). NMR (solid-state NMR or SSNMR) spectra were obtained using a Varian Unity 400 MHz spectrometer operating at a carbon frequency of 100.580 MHz, equipped with a complete solids accessory and Varian 7 mm VT CP/MAS probe. Acquisition parameters were are follows: 90° proton r.f. pulse width 4.0 μs, contact time 1.0 ms, pulse repetition time 5 s, MAS frequency 7.0 kHz, spectral width 50 kHz, and acquisition time 50 ms. Chemical shifts were referenced to the methyl group of external hexamethylbenzene (δ=17.3 ppm), that is, by sample replacement with hexamethylbenzene.

Chemical shift data for (N)-((S)-2-hydroxy-3-methyl-butyryl)-1-(L-alaninyl)-(S)-1-amino-3-methyl-2,3,4,5-tetrahydro-1H-3-benzazepin-2-one in solution (based on the peak assignments, below) is shown in Table 2.

TABLE 2

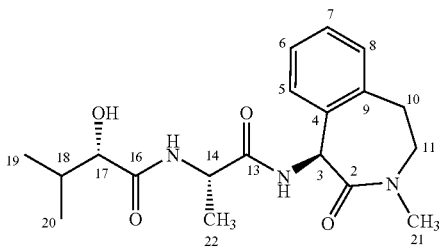

| Site | Solution in DMSO | Anhydrate Form-α (solid) |
|---|---|---|
| 2, 13, 16 | 169.27, 171.73, 172.89 | 168.6*, 169.5*, 170.6*, 172.7*, 175.4*, 177.8* |
| 3, 11, 14 | 51.45, 47.05, 47.72 | 48.0, 50.7, 51.2, 52.3 |
| 4 | 134.14 | 132.4* |
| 5, 6 | 124.18, 125.99 | 122.6, 122.9, 123.6 |
| 7 | 127.19 | 126.8, 127.4, 128.1, 128.7 |
| 8 | 130.38 | 131.2, 131.7 |
| 9 | 135.32 | 135.5*, 136.3* |
| 10, 18 | 30.73, 31.29 | 29.8, 33.3 |
| 17 | 75.01 | 77.9, 79.0 |
| 19, 20, 22 | 15.99, 18.66, 19.13 | 14.6*, 16.9*, 20.3*, 21.2*, 21.9* |
| 21 | 34.18 | 32.7*, 36.2*, 37.8* |

Asterisks (*) denote peaks appearing in the interrupted decoupling spectrum.

Thus, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-α may be characterized by solid state $^{13}C$ nuclear magnetic resonances in the table above.

A further aspect of the present invention is directed to crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β characterized by the X-ray powder diffraction patterns in Table 3, which lists the 2θ values and relative intensities ($I_0/I_{100}$) greater than 20% measured for an unground sample using the methodology described above with $CuK_\alpha$ radiation:

TABLE 3

| Unground | | 5 min grinding | |
|---|---|---|---|
| 2θ (°) | $I_0/I_{100}$(%) | 2θ (°) | $I_0/I_{100}$(%) |
|  |  | 4.854 | 44.9 |
| 8.102 | 40.8 | 8.100 | 34.5 |
| 9.137 | 100.0 | 9.138 | 100.0 |
| 10.655 | 28.2 | 10.664 | 44.4 |
| 17.189 | 30.5 | 17.204 | 24.2 |

It should also be noted that the computer-generated, unrounded numbers are listed in this table.

Thus, a properly prepared crystalline sample of (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β may be characterized by X-ray diffraction pattern in 2θ values using $CuK_\alpha$ radiation having peaks as described in Table 3, and in particular having a peak at 8.10 or 10.66 (2θ±0.20); peaks at any two of 8.10, 9.14, and 10.66 (2θ±0.2°); or having peaks at 8.10, 9.14, and 10.66 (2θ±0.2°).

Crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β may also be characterized by solid state NMR spectroscopy. Solid state $^{13}C$ chemical shifts reflect not only the molecular structure of but also the electronic environment of the molecule in the crystal.

Solid state NMR ($^{13}C$) analysis can be carried out using $^{13}C$ Cross polarization/magic angle spinning (CP/MAS). The NMR (solid-state NMR or SSNMR) spectra for crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β were obtained using a Varian Unity Inova 400 MHz spectrometer operating at a carbon frequency of 100.578 MHz, equipped with a complete solids accessory and Chemagnetics 4.0 mm T3 probe. Acquisition parameters were as follows: 90° proton r.f. pulse width 4.0 μs, contact time 1.5 ms, pulse repetition time 5 s, MAS frequency 7.0 kHz, spectral width 50 kHz, and acquisition time 50 ms. Chemical shifts were referenced to the methyl group of external hexamethylbenzene (δ=17.3 ppm), that is, by sample replacement with hexamethylbenzene. Thus, crystalline (N)-((S)-2-hydroxy-3-methyl-butyryl)-1-(L-alaninyl)-(S)-1-amino-3-methyl-2,3,4,5-tetrahydro-1H-3-benzazepin-2-one anhydrate Form-β may be characterized by the following solid state $^{13}C$ nuclear magnetic resonances: 19.1, 77.2, or 130.5+/−0.1 ppm; more particularly at any two of 19.1, 77.2, and 130.5+/−0.1 ppm; or at 19.1, 77.2, and 130.5+/−0.1 ppm.

Another aspect of the present invention is directed to crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate characterized by the X-ray powder diffraction patterns in Table 4, which lists the 2θ values and relative intensities ($I_0/I_{100}$) greater than 20%, measured for an unground sample and for a samples after 5 and 10 minutes of grinding and using the methodology described above with $CuK_\alpha$ radiation:

TABLE 4

| Unground | | 5 min grinding | | 10 min grinding | |
|---|---|---|---|---|---|
| 2θ (°) | $I_0/I_{100}$(%) | 2θ (°) | $I_0/I_{100}$(%) | 2θ (°) | $I_0/I_{100}$(%) |
| 8.361 | 100 | 8.349 | 87.6 | 8.367 | 88.7 |
| 12.433 | 51.4 | 12.429 | 78.5 | 12.424 | 91.6 |
|  |  | 13.24 | 27.9 | 13.254 | 30.4 |
| 15.344 | 49.8 | 15.336 | 100 | 15.352 | 100 |
|  |  | 16.858 | 28.5 | 16.88 | 28.3 |
| 19.224 | 27.9 | 19.233 | 47.8 | 19.24 | 52 |
| 20.495 | 27.5 | 20.48 | 44.4 |  |  |
| 20.63 | 38.8 | 20.644 | 43 | 20.601 | 48.9 |
|  |  | 22.254 | 19.5 | 22.045 | 21.6 |
|  |  | 22.63 | 27.6 | 22.654 | 34.9 |
|  |  | 24.388 | 26.4 | 23.388 | 19.7 |
|  |  |  |  | 24.387 | 28.2 |
|  |  |  |  | 27.744 | 19 |
|  |  |  |  | 22.237 | 21.2 |

The intensities of the samples ground for 5 and 10 minutes are more representative of the diffraction pattern where attempts were made to minimize the effects of preferred orientation and/or particle size. It should also be noted that the computer-generated, unrounded numbers are listed in this table.

Thus, a properly prepared crystalline sample of (N)-((S)-2-hydroxy-3-methyl-butyryl)-1-(L-alaninyl)-(S)-1-amino-3-methyl-2,3,4,5-tetrahydro-1H-3-benzazepin-2-one dihydrate may be characterized by X-ray diffraction pattern in 2θ values using $CuK_\alpha$ radiation having peaks as described in Table 4, and in particular having a peak at 8.36, 12.43, 15.34, 19.22, 20.50, or 20.63; more particularly having a peak at 8.36, 12.43, or 15.34; peaks at 8.36 and 12.43; 8.36 and 15.34; 8.36, 12.43, and 15.34; or at 8.36, 12.43, 15.34, 19.22, 20.50, and 20.63.

Crystalline (N)-((S)-2-hydroxy-3-methyl-butyryl)-1-(L-alaninyl)-(S)-1-amino-3-methyl-2,3,4,5-tetrahydro-1H-3-benzazepin-2-one dihydrate may also be characterized by solid state NMR spectroscopy. Solid state $^{13}$C chemical shifts reflect not only the molecular structure of but also the electronic environment of the molecule in the crystal.

Solid state NMR ($^{13}$C) analysis can be carried out using $^{13}$C Cross polarization/magic angle spinning (CP/MAS). NMR (solid-state NMR or SSNMR) spectra were obtained using a Varian Unity 400 MHz spectrometer operating at a carbon frequency of 100.580 MHz, equipped with a complete solids accessory and Varian 7 mm VT CP/MAS probe. Acquisition parameters were are follows: 90° proton r.f. pulse width 4.0 μs, contact time 1.0 ms, pulse repetition time 5 s, MAS frequency 7.0 kHz, spectral width 50 kHz, and acquisition time 50 ms. Chemical shifts were referenced to the methyl group of external hexamethylbenzene (δ=17.3 ppm), that is, by sample replacement with hexamethylbenzene.

Chemical shift data for (N)-((S)-2-hydroxy-3-methyl-butyryl)-1-(L-alaninyl)-(S)-1-amino-3-methyl-2,3,4,5-tetrahydro-1H-3-benzazepin-2-one dihydrate (based on the peak assignments, below) are shown in Table 5.

TABLE 5

| Site | Solution in DMSO | Dihydrate (solid) |
|---|---|---|
| 2, 13, 16 | 169.27, 171.73, 172.89 | 169.9*, 174.1*, 176.7* |
| 3, 11, 14 | 51.45, 47.05, 47.72 | 46.9, 51.3 |
| 4 | 134.14 | 134.8* |
| 5, 6 | 124.18, 125.99 | 124.0 |
| 7 | 127.19 | 127.9, 128.9 |
| 8 | 130.38 | 132.1 |
| 9 | 135.32 | 136.9* |
| 10, 18 | 30.73, 31.29 | 31.1 |
| 17 | 75.01 | 75.6 |
| 19, 20, 22 | 15.99, 18.66, 19.13 | 16.6*, 21.4* |
| 21 | 34.18 | 35.3* |

Asterisks (*) denote peaks appearing in the interrupted decoupling spectrum.

Thus crystalline (N)-((S)-2-hydroxy-3-methyl-butyryl)-1-(L-alaninyl)-(S)-1-amino-3-2,3,4,5-tetrahydro-1H-3-benzazepin-2-one dihydrate may be characterized by solid state $^{13}$C nuclear magnetic resonance having chemical shift (ppm) of 16.6; 176.7, 174.1, 169.9, 136.9, 134.8, 132.1, 127.9, 128.9, 124.0, 75.6, 51.3, 46.9, 35.3, 31.1, 21.4, or 16.6; more particularly, 75.6, 35.3, 21.4, or 16.6; any two of 75.6, 35.3, 21.4, and 16.6; 75.6, 35.3, 21.4, and 16.6; or at 176.7, 174.1, 169.9, 136.9, 134.8, 132.1, 127.9, 128.9, 124.0, 75.6, 51.3, 46.9, 35.3, 31.1, 21.4, and 16.6.

The present invention is further illustrated by the following examples and preparations. These examples and preparations are illustrative only and are not intended to limit the invention in any way.

The terms used in the examples and preparations have their normal meanings unless otherwise designated. For example "° C." refers to degrees Celsius; "mmol" refers to millimole or millimoles; "g" refers to gram or grams; "mL" refers to milliliter or milliliters; "brine" refers to a saturated aqueous sodium chloride solution; "THF" refers to tetrahydrofuran; "HPLC" refers to high pressure liquid chromatography; "DSC" refers to differential scanning calorimetry; etc.

EXAMPLE 1

Synthesis of 1-amino-3-methyl-2,3,4,5-tetrahydro-1H-3-benzazepin-2-one

To a slurry of sodium hydride (1.1 eq) in 15 mL of dry DMF was added 2,3,4,5-tetrahydro-1H-3-benzazepin-2-one (0.0042 moles) as a solution in 10 mL of DMF. Methyl iodide (about 2 eq.) was then added. When complete by TLC, the reaction mixture was poured over ice and extracted into ethyl acetate. The organic layer was washed with water, followed by brine. The organic layer was then dried over Na$_2$SO$_4$, filtered, and concentrated under reduced pressure. The residue was purified by HPLC (LC 2000), eluting with an ethyl acetate/hexane system to give 3-methyl-2,3,4,5-tetrahydro-1H-3-benzazepin-2-one.

3-Methyl-2,3,4,5-tetrahydro-1H-3-benzazepin-2-one (1 eq.) was dissolved in THF and isoamylnitrite (1.2 eq.) was added. The mixture was cooled to 0° C. in an ice bath. NaHMDS (1.1 eq., 1M in THF) was added dropwise. After stirring for 1 hour or until the reaction was complete, the mixture was concentrated then acidified with 1N aqueous hydrochloric acid solution and extracted with ethyl acetate. The organic portion was dried and concentrated to yield a crude product which was purified by silica gel chromatography to give 1-hydroxyimino-3-methyl-2,3,4,5-tetrahydro-1H-3-benzazepin-2-one: Mass spectroscopy (M+H)$^+$, 205.1.

1-Hydroxyimino-3-methyl-2,3,4,5-tetrahydro-1H-3-benzazepin-2-one was dissolved in EtOH/NH$_3$ (20:1) and hydrogenated in a bomb using Raney nickel and hydrogen (500 psi/3447 kPa) at 100° C. for 10 hours. The resulting mixture was filtered and concentrated to provide an oil which was purified by silica gel chromatography to yield the title compound.

EXAMPLE 2

Synthesis of 1-amino-3-methyl-2,3 4,5-tetrahydro-1H-3-benzazepin-2-one

To a 20 L Morton flask was added MTBE (5.52 L, 7 volumes) and (N-methyl-amino)-acetaldehyde dimethyl acetal (614 g, 5 mol) to form a solution at room temperature. A solution of sodium bicarbonate prepared by the addition of sodium bicarbonate (546 g, 6.5 mol) and water (6.31 L, 8 volume) was added to the Morton reaction flask. The mixture was cooled to less than 10° C and a MTBE (789 mL) solution of phenylacetyl chloride (789 g, 5 mol) was added dropwise to the cooled reaction mixture over a 1 h period. After addition, the reaction mixture was stirred at room temperature for 1 h. At this stage an HPLC analysis indicated that the reaction was completed. Extractive workup with MTBE (4 volumes), anhydrous magnesium sulfate drying followed by concentration on the rotary evaporator provided 1.187 kg (98%) of N-methyl-N-(2,2-dimethoxyethyl)phenylacetamide as a liquid, (M+H)$^+$=237.9.

To a 5 L Morton flask under a strong nitrogen atmosphere was added H$_2$SO$_4$, (1.42 L) and N-methyl-N-(2,2- dimethoxyethyl)phenylacetamide (712 g, 3 mol) was added dropwise to the reaction flask which caused an exotherm (22 to 78° C.). The resulting reaction was then heated to 110° C. for 3 h then cooled to room temperature and transferred to a 20 L Morton flask. At less than 10° C., the reaction mixture was quenched with aqueous sodium hydroxide (9.18 L, 5 N). Extractive workup with ethyl acetate (2×2.85 L), drying with sodium sulfate followed by concentrating to a solid, provided 520 g (73.5%) of 3-methyl-2,3-dihydro-1H-3-benzazepin-2-one as a solid. This material may be recrystallized from MTBE for added purity to give a solid, mp=81-82° C.; $(M+H)^+=174.2$.

A THF (0.5 L) solution of 3-methyl-2,3-dihydro-1H-3-benzazepin-2-one (113.8 g, 0.657 mol) was cooled to 0° C. and isoamyl nitrite (100.75 g, 0.86 mol) was added dropwise. To the resulting mixture was added LiHMDS (1 N THF solution, 854 mL, 0.854 mol) at a rate such that the temperature remained below 10° C. After addition, the reaction was allowed to stir at room temperature for 2-3 h while monitoring for the reaction progress by HPLC. Upon completion of the reaction, the mixture was cooled to 0° C., and the pH adjusted from 12 to 2-3 using aqueous HCl (2N). The resulting precipitate was stirred for 12-16 h before isolation by filtration and drying to provide 86.3 g (64.9%) of 1-hydroxyimino-3-methyl-2,3-dihydro-1H-3-benzazepin-2-one; mp=225-226° C.; $(M+H)^+=203.0$.

An ethanol (525 mL) solution of 1-hydroxyimino-3-methyl-2,3-dihydro-1H-3-benzazepin-2-one (35 g, 0.173 mol) was added to an autoclave along with palladium on carbon (10%, 3.5 g) as a dilute HCl (concentrated aqueous, 17.5 g in 17 mL water) slurry. The resulting mixture was hydrogenated at 50° C. and 250 psi (1723 kPa) until the reaction was completed. The reaction mixture was filtered over a pad of celite using ethanol as solvent and the filtrate concentrated to 90 mL. Water (350 mL) was added to the concentrate and the resulting solution further concentrated to about 200 μL. Dichloromethane (350 mL) was added to the aqueous solution before adjusting the pH to 11-11.5 with aqueous sodium hydroxide (1 N). The organic portion was separated and the aqueous portion extracted with dichloromethane (175 mL). The combined extracts were concentrated to a residue that crystallized upon standing to give the title compound: mp=69-81° C.; (M+H)+=191.0.

EXAMPLE 3

Synthesis of 1-amino-3-methyl-2,3,4,5-tetrahydro-1H-3-benzazepin-2-one

To a 22 L Morton flask was added dichloromethane (4.73 L, 8 volumes), N-methylphenethylamine (591 g, 4.33 mol), and aqueous sodium bicarbonate (436.7 g, 5.2 mol in 4.73 L of water). The mixture was cooled to less than 5° C. and dichloromethane (887 mL) solution of chloroacetyl chloride (513.7 g, 4.55 mol) was added dropwise to the cooled reaction mixture over a 70 min period. After addition, an HPLC analysis indicated that the reaction was completed. The layers were separated and the aqueous layer was extracted with dichloromethane. Combined organic layers were dried over anhydrous magnesium sulfate and concentrated on the rotary evaporator to provide 915.7 g (99.8%) of N-methyl-N-(2-phenylethyl)-1-chloroacetamide: (M+H)=212.1.

To a 12 L flask under a nitrogen atmosphere was added N-methyl-N-(2-phenylethyl)-1-chloroacetamide (883.3 g, 4.17 mol) and ortho-dichlorobenzene (6.18 L). Add aluminum chloride (1319 g, 10.13 mol) which caused an exotherm (22 to 50° C.). The resulting reaction was then heated to 165° C. for 2.5 h then cooled to room temperature over about 14 hours. The reaction mixture was cooled to about 0° C., and was added to cold water (8.86 L, about 5° C.) in four portions in order to keep exotherm to about 40° C. The layers were separated and aqueous layer was extracted with dichloromethane (7.07 L) and the layers separated. The organic layers were combined and extracted with aqueous hydrochloric acid (8.83 L, 1N) and then a saturated aqueous sodium bicarbonate solution (7.07 L), dried over magnesium sulfate, combined with silica gel (883 g) and applied to a column of silica gel (3.53 kg, in a sintered glass funnel, packed as a slurry in dichloromethane). The column was eluted with dichloromethane until 25 L were collected and then with ethyl acetate to provide the product. The product containing fraction were evaporated to 3-methyl-2,3,4,5-tetrahydro-1H-3-benzazepin-2-one as a tan solid, 608 g (83%).

In a 22 L flask, under nitrogen, was 3-methyl-2,3,4,5-tetrahydro-1H-3-benzazepin-2-one (606 g, 3.46 mol) and isoamyl nitrite (543 g, 4.5 mol) in THF (7.88 L). The mixture was cooled to about 0° C. before LiHMDS (1 N THF solution, 4.5 L, 04.5 mol) was added at a rate such that the temperature remained below about 7° C. After addition, the reaction was allowed to stir at room temperature for about 2 h while monitoring for the reaction progress by HPLC. Upon completion of the reaction, the mixture was cooled to about 0° C., and the pH adjusted from 12 to about 2-1 using aqueous HCl (2N). The resulting precipitate was stirred for about 6 h before isolation by filtration and drying to provide 1-hydroxyimino-3-methyl-2,3,4,5-tetrahydro-1H-3-benzazepin-2-one 604.7 g (85.6%).

1-Hydroxyimino-3-methyl-2,3,4,5-tetrahydro-1H-3-benzazepin-2-one (625 g, 3.06 mol) and 3A ethanol (15.6 L), was added to an autoclave along with palladium on carbon (10%, 120 g) as a as a dilute HCl (concentrated aqueous hydrochloric acid (312 g in 320 mL water) slurry. The resulting mixture was hydrogenated at 50° C. and 250 psi (1723 kPa) with vigorous agitation until the reaction was completed (about 4 hours). The reaction mixture was filtered over a pad of celite using ethanol as solvent and the filtrate concentrated give a solid. The solid was treated with dichloromethane (6 L) and 1N aqueous sodium hydroxide solution was added until the pH to of the aqueous layer was between 11-11.5. The mixture was agitated, the layers were separated, and the aqueous layer was extracted with dichloromethane (2 L). The organic layers were dried over magnesium sulfate, filtered, and evaporated in a rotary evaporator to give the title compound 477 g (81.9%).

EXAMPLE 4

Synthesis of (S)-1-amino-3-methyl-2,3,4,5-tetrahydro-1H-3-benzazepin-2-one

1-Amino-3-methyl-2,3,4,5-tetrahydro-1H-3-benzazepin-2-one (1.544 g, 8.12 mmol) was heated gently in 15 mL methanol to form a solution. In another flask, di-p-toluoyl-1-tartaric acid (3.12 g, 8.08 mmol) was dissolved in 15 mL methanol and added via pipette to the warm amine solution. The mixture was heated as solids precipitated. An additional 30 mL of methanol was added to achieve a solution, which was refluxed for 30-40 minutes and then slowly cooled to ambient temperature to give a solid. After stirring for about 18 hours, the solid was collected by filtration and rinsed with a small amount of cold methanol to give 2.24 g of (S)-1-amino-3-methyl-2,3,4,5-tetrahydro-1H-3-benzazepin-2-one di-p-toluoyl-L-tartaric acid salt (96% yield, 94.7% ee).

(S)-1-Amino-3-methyl-2,3,4,5-tetrahydro-1H-3-benzazepin-2-one di-p-toluoyl-L-tartaric acid salt (11.83 g, 20.5 mmol) was dissolved in 45 mL of aqueous 1.0 N sodium hydroxide solution and extracted with methylene chloride (3×25 mL). The combined methylene chloride layers were washed with 35 mL aqueous 1.0 N sodium hydroxide solution, then brine solution, and dried over anhydrous $MgSO_4$. Removal of solvent under vacuum gave the title compound (3.38 g) as a colorless oil (87% yield, 93.2% ee).

EXAMPLE 5

Synthesis of (S)-1-amino-3-methyl-2,3,4,5-tetrahydro-1H-3-benzazepin-2-one

1-Amino-3-methyl-2,3,4,5-tetrahydro-1H-3-benzazepin-2-one (6.0 g, 31.5 mmol) was heated gently in 75 mL methanol to form a solution and combined with a solution of di-p-toluoyl-L-tartaric acid (12.2 g, 31.5 mmol) in 75 mL of warm methanol. The solution was seeded and a solid formed. An additional 100 mL of methanol was added and the mixture was allowed to stir. After stirring for about 18 hours, the solid was collected by filtration and rinsed with a small amount of cold methanol to give 6.7 g of a solid. The solid was combined with methanol (200 mL), and stirred. After 18 hours, the solid was collected to give (S)-1-amino-3-methyl-2,3,4,5-tetrahydro-1H-3-benzazepin-2-one di-p-toluoyl-L-tartaric acid salt (4.4 g). Isolation of the base by the procedure described in Example 4 gave the title compound (96% ee).

EXAMPLE 6

Synthesis of (S)-1-amino-3-methyl-2,3,4,5-tetrahydro-1H-3-benzazepin-2-one

In a 22 L vessel, under nitrogen, 1-amino-3-methyl-2,3,4,5-tetrahydro-1H-3-benzazepin-2-one (438 g, 2.3 mol) was heated (about 40° C.) to provide a solution in methanol (4.38 mL). In another flask, di-p-toluoyl-l-tartaric acid (889.7 g, 2.3 mol) was dissolved in 4.38 L of methanol and heated to about 40° C. before the solution of 1-amino-3-methyl-2,3,4,5-tetrahydro-1H-3-benzazepin-2-one was added. The heating was continued and an additional 6.13 L of methanol was added before the mixture was refluxed for about 45 minutes and then slowly cooled to ambient temperature to give a solid. After stirring for about 18 hours, the solid was collected by filtration and rinsed with a small amount of mother liquors, and after air drying, with about 2 L of ethyl acetate to give 561.6 g of (S)-1-amino-3-methyl-2,3,4,5-tetrahydro-1H-3-benzazepin-2-one di-p-toluoyl-L-tartaric acid salt. Combine (S)-1-amino-3-methyl-2,3,4,5-tetrahydro-1H-3-benzazepin-2-one di-p-toluoyl-L-tartaric acid salt, dichloromethane (6.57 L) and 1N aqueous sodium hydroxide solution (6.57 L) and agitate. Separate the layers and extract the organic layer twice with and 1N aqueous sodium hydroxide solution (3.28 L), once with brine (2.46 L) before drying over magnesium sulfate, filtering, and evaporating on a rotary evaporator to give the title compound 250g (57.4%, 94.1% ee).

EXAMPLE 7

Synthesis of (S)-1-amino-3-methyl-2,3,4,5-tetrahydro-1H-3-benzazepin-2-one hydrochloric acid salt 1-Amino-3-methyl-2,3,4,5-tetrahydro-1H-3-benzazepin-2-one (31.9 g, 168 mmol) was slurried in about 300 mL isopropyl acetate and heated to 45° C. In a separate flask, (R)-(−)-D-mandelic acid (25.0 g, 164 mmol) was heated in about 130 mL of isopropyl alcohol until a solution formed and was added to the 1-amino-3-methyl-2,3,4,5-tetrahydro-1H-3-benzazepin-2-one/isopropyl acetate slurry obtained above to give a solution from which a precipitate quickly formed. The mixture was stirred at 45° C. for about 3 hours. 5-Nitrosalicylaldehyde (2-hydroxy-5-nitrobenzaldehyde) (1.40 g, 8.38 mmol, 5 mol %) was added to the warm solution and the mixture was stirred at 45° C. After about 14 hours, the slurry was cooled to ambient temperature and stirred for 2 hours before the solids were collected by filtration and rinsed with 70 mL of cold isopropyl acetate, and dried in the vacuum oven at 40° C. to obtain 46.62 g of (S)-1-amino-3-methyl-2,3,4,5-tetrahydro-1H-3-benzazepin-2-one (R)-mandelic acid salt (82.9% yield, 98.4% ee).

(S)-1-Amino-3-methyl-2,3,4,5-tetrahydro-1H-3-benzazepin-2-one (R)-mandelic acid salt (2.42 g, 7.06 mmol, 98.4% ee) was slurried in 25 mL ethyl acetate at ambient temperature. Concentrated aqueous hydrochloric acid (1.1 mL, about 11.2 mmol) was added and the mixture was heated to 50° C. with vigorous stirring for 3.5 hours. The slurry was cooled to ambient temperature and filtered, rinsed with the methyl t-butyl ether (about 10 mL) to give 1.48 g of the title compound (92.5% yield, 97.9% ee).

EXAMPLE 8

Synthesis of (N)-((S)-2-hydroxy-3-methyl-butyryl)-1-(L-alaninyl)-(S)-amino-3-methyl-2,3,4,5-tetrahydro-1H-3-benzazepin-2-one A round bottom flask was charged with N-t-Boc-L-alanine (1.0 eq.), hydroxy-benzotriazole hydrate (about 1.1 eq.) and (S)-1-amino-3-methyl-2,3,4,5-tetrahydro-1H-3-benzazepin-2-one (1.0 eq.) in THF under nitrogen atmosphere. Hunig's base (N,N-diisopropylethylamine, 1.1 eq.) was added to the well stirred mixture followed by EDC (1.1 eq.). After stirring from 4 to 17 hours at ambient temperature the solvent was removed at reduced pressure, the residue taken up in ethyl acetate and water, washed with saturated aqueous sodium bicarbonate solution, 1 N aqueous HCl, brine, dried over anhydrous sodium sulfate, filtered, and the solvent removed at reduced pressure to provide 1-(N-t-Boc-L-alaninyl)amino-3-methyl-2,3,4,5-tetrahydro-1H-3-benzazepin-2-one: mass spectroscopy $(M+H)^+$, 362.3.

A stream of anhydrous HCl gas was passed through a stirred solution of 1-(N-t-Boc-L-alaninyl)amino-3-methyl-2,3,4,5-tetrahydro-2H-3-benzazepin-2-one in 1,4-dioxane (0.03-0.09 M), chilled in a ice bath to about 10C under $N_2$, for 10-15 minutes. The solution was capped, then the cooling bath removed, and the solution was allowed to warm to ambient temperature with stirring for 2-8 hours, monitoring by TLC for the consumption of starting material. The solution was concentrated to give 1-(L-alaninyl)-(S)-amino-3-methyl-2,3,4,5-tetrahydro-1H-3-benzazepin-2-one which was used without further purification.

1-(L-Alaninyl)-(S)-amino-3-methyl-2,3,4,5-tetrahydro-3-methyl-1H-3-benzazepin-2-one (1.0 eq.), hydroxybenzotriazole hydrate (1.1 eq.) and (S)-2-hydroxy-3-methyl-butyric acid (1.0 eq.) in THF under nitrogen atmosphere. Hunig's base (N,N-diisopropyl-ethylamine, 1.1 eq.) was added to the well stirred mixture followed by EDC (1.1 eq). After stirring from 4 to 17 hours at ambient temperature the solvent was removed at reduced pressure, the residue taken up in ethyl acetate (or similar solvent) and water, washed with saturated aqueous sodium bicarbonate solution, 1 N HCl, brine, dried over anhydrous sodium sulfate and the solvent removed at reduced pressure to provide the title compound.

EXAMPLE 9

Synthesis of (N)-((S)-2-hydroxy-3-methyl-butyryl)-1-(L-alaninyl)-(S)-amino-3-methyl-2,3,4,5-tetrahydro-1H-3-benzazepin-2-one A round bottom flask was charged with N-t-Boc-L-alanine (249.5 g, 1.32 mol), hydroxybenzotriazole hydrate (232.2 g, 1.52 mol), and (S)-1-amino-3-methyl-2,3,4,5-tetrahydro-1H-3-benzazepin-2-one (250.8 g, 1.32 mol) in THF (3.76 L) under nitrogen atmosphere. The mixture was cooled to less than 5° C. before adding Hunig's base (N,N-diisopropylethylamine, 188.4 g, 1.45 mol) followed by EDC (283.7 g, 1.45 mol). After stirring 6 hours the reaction mixture was warmed to ambient temperature and stirred for about 14 hours. The solvent was removed at reduced pressure, the residue taken up in ethyl acetate (3.76 L) and water (1.76 L), the layers were separated, the organic layer extracted with water (1.76 L), the aqueous layers combined and extracted with ethyl acetate (1.76 L). The organic layers were combined, extracted with saturated aqueous sodium bicarbonate solution (1.76 L), dried over anhydrous sodium sulfate, filtered, and evaporated in on a rotary evaporator to provide 1-(N-t-Boc-L-alaninyl) amino-3-methyl-2,3,4,5-tetrahydro-1H-3-benzazepin-2-one 463 g (97.2%).

An ethyl acetate solution of HCl was prepared by passing anhydrous HCl gas, using a subsurface dispersion tube, through ethyl acetate (1.76 L) cooled to about 0° C. The ethyl acetate solution of HCl prepared above was added to a vigorously stirred slurry of 1-(N-t-Boc-L-alaninyl)amino-3-methyl-2,3,4,5-tetrahydro-1H-3-benzazepin-2-one (462 g, 1.28 mol) in ethyl acetate (3.7 L). An additional amount of ethyl acetate (1 L) was added and the reaction mixture was allowed to warm to room temperature and stirred for 22 h. The reaction mixture was filtered to give a solid. The solid was slurryed with acetonitrile (5 L), heated to reflux and then cooled to about 60° C. before filtering and drying to give 1-(L-alaninyl)-(S)-amino-3-methyl-2,3,4,5-tetrahydro-1H-3-benzazepin-2-one 389.8 g (94.7%).

1-(L-Alaninyl)-(S)-amino-3-methyl-2,3,4,5-tetrahydro-3-methyl-1H-3-benzazepin-2-one (369.5 g, 1.18 mol), hydroxybenzotriazole hydrate (207.6 g, 1.36 mol), Hunig's base (N,N-diisopropylethylamine, 352.2 g, 2.71 mol), and (S)-2-hydroxy-3-methyl-butyric acid (140.6 g, 1.18 mol) in THF (4.8 L) were combined under a nitrogen atmosphere and cooled to less than 5° C. EDC (253.7 g, 1.3 mol) was added and the reaction mixture was allowed to warm to ambient temperature and to stir. After about 25 hours the reaction mixture was diluted with dichloromethane (5.54 L) and extracted with water (2.22 L). The organic layer was extracted with water (2.22 L), the aqueous layers were combined and extracted with dichloromethane (5.54 L). The organic layers were combined, extracted twice with water (2.22 L), with saturated aqueous sodium bicarbonate solution (2.22 L), dried over anhydrous sodium sulfate, filtered, and evaporated in on a rotary evaporator to provide the title compound 428g (100%).

EXAMPLE 10

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one dihydrate (N)-((S)-2-Hydroxy-3-methyl-butyryl)-1-(L-alaninyl)-(S)-amino-3-methyl-2,3,4,5-tetrahydro-1H-3-benzazepin-2-one solid (428 g) was taken up in acetone (3.42 L) and water (0.856 L) with slight warming (40° C.). The solution was split into ~2 L portions and to each was added water (7.19 L) while warming the hazy solution to 50° C. Upon complete addition of water the hazy solution was allowed to cool to ambient to give a solid which was stirred as a slurry at ambient temperature for about 14 hours before filtering and drying to give the title compound 310.6 g (66.2%).

EXAMPLE 11

1-(L-alaninyl)-(S)-amino-3-methyl-2,3,4,5-tetrahydro-1H-3-benzazepin-2-one methanesulfonate To a 250-mL 3-necked round bottomed flask equipped with a thermocouple, nitrogen purge and a magnetic stir bar was charged t-Boc-L-alanine (21.91 g, 0.116 M) and THF (150 mL). Upon stirring the solids dissolved, cooled contents in a water bath to about 22° C. N-methylmorpholine (11.71 g, 0.116M) was added over 2 minutes and stirred for 15 minutes. This solution was added over 15 minutes to a solution of isobutyl chloroformate (15.52 g, 0.114M) in THF (90 mL) at about 2° C. The reaction mixture was cooled back to 0 to 5° C., and stirred for 30 minutes.

To this mixed anhydride solution was added (S)-1-amino-3-methyl-2,3,4,5-tetrahydro-1H-3-benzazepin-2-one (25 g, 0.110M) in one portion through a funnel. Rinsed the funnel with 50 mL THF and added to the acylation reaction mixture. This was followed by addition of N-methylmorpholine (11.15g, 0.110 M) and an exotherm (10° C.) was observed. The slurry was allowed to rise to ambient temperature and stirred for 30 minutes. To the reaction mixture was added 250 mL 20% w/v aqueous sodium chloride over 10 minutes, stirred for 15 minutes, and layers separated.

Transferred the organic layer into 1 L 3-necked round bottomed flask equipped with a mechanical agitator, heating mantle, thermocouple, condenser, and nitrogen purge. Added water (37.5 mL), followed by methanesulfonic acid (15.9 g, 0.165M). Raised temperature to 62° C., maintained there for 18 h. Cooled contents to 52° C., added 275 mL acetone over ~1 h keeping temperature at 50-52° C. The slurry was stirred for an additional 1 h at this temperature, cooled to ambient temperature and stirred for 2 h. Filtered and rinsed with 75 mL acetone. Product was suction dried and then vacuum dried at 55° C. overnight to give 37g (93.87%) of a white product.

$^1$H NMR (DMSO-$d_6$): δ1.39 (d, 3H, C$\underline{H}_3$), 2.28 (S, 3H, —OSO$_2$CH$_3$), 2.92 (S, 3H, —NC$\underline{H}_3$), 2.91 (m, 2H, 2×C$\underline{H}$), 3.81 (m, 1H, CH), 4.23 (m, 2H, 2×C$\underline{H}$), 6.21 (d, 1H, C$\underline{H}$), 7.18 (m, 4H, aromatic C$\underline{H}$), 8.10 (broad, 3H, $^+$N$\underline{H}_3$), 8.94 (d, 1H, —CON$\underline{H}$).

EXAMPLE 12

1-(L-alaninyl)-(S)-amino-3-methyl-2,3,4,5-tetrahydro-1H-3-benzazepin-2-one hydrochloride To a 250-mL 3-necked round bottomed flask equipped with a thermocouple, nitrogen purge and a magnetic stir bar was charged t-Boc-L-alanine (21.91 g, 0.116 M) and THF (150 mL). Upon stirring the solids dissolved, cooled contents in a water bath to about 22° C. N-methylmorpholine (11.71 g, 0.116M) was added over 2 minutes and stirred for 15 minutes. This solution was added over 15 minutes to a solution of isobutyl chloro-formate (15.52 g, 0.114M) in THF (90 mL) at about 2° C. The reaction mixture was cooled back to 0 to 5° C., and stirred for 30 minutes.

To this mixed anhydride solution was added (S)-1-amino-3-methyl-2,3,4,5-tetrahydro-1H-3-benzazepin-2-one (25g, 0.110M) in one portion through a funnel. Rinsed the funnel with 50 mL THF and added to the acylation reaction mixture. This was followed by addition of N-methylmorpholine (11.15 g, 0.110 M) and an exotherm (10° C.) was observed. The slurry was allowed to rise to ambient temperature and stirred for 30 minutes. To the reaction mixture was added 250 mL 20% w/v aqueous sodium chloride over 10 minutes, stirred for 15 minutes, and layers separated.

Transferred the organic layer into 1 L 3-necked round bottomed flask equipped with a mechanical agitator, heating mantle, thermocouple, condenser, and nitrogen purge. With a setpoint of 90° C. removed THF and exchanged it with 375 mL acetonitrile, distillation continued until about 11.5 volumes of solvent was left in the pot and pot temperature reached 83° C. Solution turned hazy, cooled contents to 38° C., added concentrated HCl (18.5 mL), temperature rose to 45° C. Homogenous solution was formed, raised temperature to 65° C., maintained there for 2 h. The reaction mixture was cooled to ~52° C., and then acetonitrile (340 mL) was added over about 1.5 h, maintaining the reaction temperature at 50 to 52° C. With a setpoint of 90° C., distillation was conducted removing about 125 mL acetonitrile. The resulting slurry was cooled to 50° C., maintained there for 1 h, then cooled to ambient temperature, stirred overnight at ambient temperature. Filtered and rinsed with 75 mL acetonitrile. Product was suction dried and then vacuum dried at 55° C. overnight to give 30.4 g (92.57%) of white product.

$^1$H NMR (DMSO-$d_6$): δ1.39 (d, 3H, —C$\underline{H}_3$), 2.92 (S, 3H, —NC$\underline{H}_3$), 3.19 (m, 2H, 2×C$\underline{H}$), 3.39 (m, 2H, 2×C$\underline{H}$), 4.36 (m, 2H, 2×C$\underline{H}$), 6.20 (d, 1H, C$\underline{H}$), 7.21 (m, 4H, aromatic CH), 8.27 (broad, 3H, -$^+$N$\underline{H}_3$), 9.01 (d, 1H, —CON$\underline{H}$)

EXAMPLE 13

(N)-((S)-2-hydroxy-3-methyl-butyryl)-1-(L-alaninyl)-(S)-amino-3-methyl-2,3,4,5-tetrahydro-1H-3-benzazepin-2-one dihydrate A mixture of (S)-2-hydroxy-3-methyl-butyric acid (20.2 g, 0.171 M), HMDS (80 mL), and NH$_4$SO$_4$ (80 mg) was heated to 124 to 126° C. where upon the solid mass dissolved to form a homogeneous solution. The solution was refluxed for 6 hr and then allowed to cool to ambient temperature overnight. The excess HMDS was removed via vacuum distillation (~47 ml, 28 to 30° C. at 1.4 to 1.7 torr). A second fraction was distilled at 40 to 45° C. (1.4 to 1.8 torr) to provide bis-trimethylsilyl-(S)-2-hydroxy-3-methyl-butyric acid (40.3 g, 90%).

$^1$H NMR (CDCl$_3$): δ3.89 (d, 1H); 2.058 (m, 1H); 0.917 (d, 1H); 0.866 (d, 3H); 0.296 (s, 9H); 0.152 (s, 9H).

A mixture of bis-trimethylsilyl-(S)-2-hydroxy-3-methyl-butyric acid (5.32 g, 20.3 mM), methylene chloride (21 mL), and DMF (3 drops) was agitated for 5 minutes at ambient temperature. Oxalyl chloride (1.77 mL, 20.3 mM) was added via syringe over 45 minutes at ambient temperature and then the reaction mixture stirred for 2 h. In a separate vessel N-methylmorpholine (4.62 mL, 42.2 mM) was added over 3 minutes to a slurry of 1-(L-alaninyl)-(S)-amino-3-methyl-2,3,4,5-tetrahydro-1H-3-benzazepin-2-one methanesulfonate (5.58 g, 15.62 mM) in methylene chloride (67 mL) at ambient temperature and the resulting mixture was agitated for 2 hrs. This slurry was then added to the acid chloride preparation flask at ambient temperature. Methylene chloride (10 ml) was used to complete the slurry transfer. The reaction was agitated at ambient temperature for 4 hrs and then water (40 mL) was added. The reactor was equipped with a Dean-Stark trap and condenser. With a internal set point of 60° C., water and methylene chloride were distilled at ambient pressure to afford a white slurry. To the slurry at 47 to 53° C. was charged a solution of water (60 mL) and acetone (10 mL). The slurry was allowed to cool to ambient temperature over 2 hrs. The slurry was filtered and the cake washed with water (20 mL). The cake was air dried for 30 min. to provide 5.28 g (85.2%) or the title compound.

EXAMPLE 14

(N)-((S)-2-hydroxy-3-methyl-butyryl)-1-(L-alaninyl)-(S)-amino-3-methyl-2,3,4,5-tetrahydro-1H-3-benzazepin-2-one dihydrate A mixture of (N)-(tert-butoxycarbonyl)-1-(L-alaninyl)-(S)-amino-3-methyl-2,3,4,5-tetrahydro-1H-3-benzazepin-2-one (10 g, 0.02767 mol, 1 eq), distilled H$_2$O (150 mL) and 37% concentrated HCl (4.10 g, 0.0415 mol, 1.5 eq) was heated to 70° C. for 3 h. The reaction solution was cooled to ambient temperature and 5N NaOH added to adjust pH=7.0 (3.4 mL). To this solution were then added 1-hydroxybenzotriazole hydrate (HOBT-H$_2$O) (4.87 g, 0.03597 mol, 1.3 eq), (S)-2-hydroxy-3-methyl-butyric acid (3.27 g, 0.02767 mol, 1 eq), and 5N NaOH to pH=7.0 (11.4 mL). The reaction mixture was stirred for 30 min, cooled to 0-10° C., and then EDCl (1-(3-dimethylaminopropyl)-3-ethyl-carbodiimide hydrochloride (EDC)) (5.83 g, 0.03044 mol, 1.1 eq) followed by 1N HCl (3.6 mL) to bring pH down to 6.13 were added. The cooling bath was removed and the reaction mixture was allowed to warm to ambient temperature with stirring for 17 h under nitrogen. The resulting suspension is filtered and rinsed with distilled water (4×75 mL). Resulting white solid was dried via vacuum air suction dry to afford the title compound in 85% yield.

EXAMPLE 15

(N)-((S)-2-hydroxy-3-methyl-butyryl)-1-(L-alaninyl)-(S)-amino-3-methyl-2,3,4,5-tetrahydro-1H-3-benzazepin-2-one dihydrate A mixture of (N)-(tert-butoxycarbonyl)-1-(L-alaninyl)-(S)-amino-3-methyl-2,3,4,5-tetrahydro-1H-3-benzazepin-2-one (14 g, 0.03873 mol, 1 eq), distilled H$_2$O (210 mL) and 37% concentrated HCl (5.73 g, 0.0581 mol, 1.5 eq) was heated to 70° C. for 4 h. The reaction solution was cooled to ambient temperature and then HOBT-H$_2$O (6.81 g, 0.05035 mol, 1.3 eq), (S)-2-hydroxy-3-methyl-butyric acid (5.03 g, 0.0426 mol, 1 eq), and N-methylmorpho-line to pH=6.88 (12.14 g) were added. The reaction mixture was heated to 35-40° C. and stirred for 30 min, and then cooled to 10-15° C. EDCI (8.17 g, 0.0426 mol, 1.1 eq) were added, the cooling bath removed, and the reaction mixture was allowed to warm to ambient temperature with stirring for 15-18 h under nitrogen. The resulting suspension is filtered and rinsed with distilled water (3×100 mL). Resulting white solid was dried via vacuum air suction dry to afford the title compound in 87% 5 yield.

EXAMPLE 16

(N)-((S)-2-hydroxy-3-methyl-butyryl)-1-(L-alaninyl)-(S)-amino-3-methyl-2,3,4,5-tetrahydro-1H-3-benzazepin-2-one dihydrate A mixture of (N)-(tert-butoxycarbonyl)-1-(L-alaninyl)-(S)-amino-3-methyl-2,3,4,5-tetrahydro-1H-3-benzazepin-2-one (5 g, 0.01383 mol, 1 eq), ethanol (25 mL) and 37% concentrated HCl (2.04 g, 0.02075 mol, 1.5 eq) was heated to 77° C. for 2.5 h. The reaction solution was cooled to ambient temperature and then HOBT-H$_2$O (2.43 g, 0.01798 mol, 1.3 eq), (S)-2-hydroxy-3-methyl-butyric acid (1.80 g, 0.01521 mol, 1.1 eq), and N-methyl-morpholine (4.34 g, 0.04287 mol, 1.1 eq) were added. The reaction mixture was stirred for 10 min at ambient temperature, and then EDCl (2.92 g, 0.01521 mol, 1.1 eq) was added. After stirring for 4 h, water (75 mL) was added over 8-10 min and the resulting slurry stirred for 5 h. The mixture was filtered and rinsed with distilled water (3×20 mL). Resulting white solid was dried via vacuum air suction dry to afford the title compound in 88% yield.

EXAMPLE 17

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-α

(N)-((S)-2-Hydroxy-3-methyl-butyryl)-1-(L-alaninyl)-(S)-amino-3-methyl-2,3,4,5-tetrahydro-1H-3-benzazepin-2-one dihydrate was taken up as a slurry in acetone. The slurry was stirred, filtered, and dried to give the title compound. m.p.=214° C. (DSC; crimped aluminum pan heated from 25-300° C. at 10° C./minute).

EXAMPLE 18

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-α

A slurry of (N)-((S)-2-hydroxy-3-methyl-butyryl)-1-(L-alaninyl)-(S)-amino-3-methyl-2,3,4,5-tetrahydro-1H-3-benzazepin-2-one dihydrate (6.0 g.) and acetone (150 mL) was heated to 52-54° C. The mixture was filtered, maintaining at 45-50° C., to remove any insoluble matter. A Dean-Stark trap was attached and the mixture heated at a set point of 60° C. to remove about 70 mL of solvent (56.2-56.9° C.). Cooled reaction mixture to 23° C. over 3 hours, and then cooled the resulting slurry to 0-5° C. over 2 hour and stirred for 1 hour at 0-5° C. The slurry was filtered, washed with 10 mL acetone, and dried under reduced pressure at room temperature to provide 4.37 g (80.4%) of the title compound.

EXAMPLE 19

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-α

A slurry of (N)-((S)-2-hydroxy-3-methyl-butyryl)-1-(L-alaninyl)-(S)-amino-3-methyl-2,3,4,5-tetrahydro-1H-3-benzazepin-2-one dihydrate (6.0 g.) and butan-2-one (135 mL) was heated to 81° C. A Dean-Stark trap was added and the mixture heated at a set point of 84° C. to remove about 55 mL of solvent (82.9° C.). The mixture was cooled to 23° C. over 3 hours, and then the resulting slurry cooled to 0-5° C. over 2 hour and stirred for 1 hour at 0-5° C. The slurry was filtered, washed with 10 mL acetone, and dried under reduced pressure at room temperature to provide 4.24 g (77.7%) of the title compound.

EXAMPLE 20

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-α

A slurry of (N)-((S)-2-hydroxy-3-methyl-butyryl)-1-(L-alaninyl)-(S)-amino-3-methyl-2,3,4,5-tetrahydro-1H-3-benzazepin-2-one dihydrate (6.0 g.) and acetone (150 mL) was heated to 52-54° C. Acetone (12 mL) was added when the temperature reached 50° C. A Dean-Stark trap was added and the mixture heated at a set point of 60° C. to remove about 70 mL of solvent (56.2-56.9° C.). The reaction mixture was cooled to 35° C. over 1 hour and heptane (60 mL) was added by syringe pump over 2 hours, maintaining the temperature at 35° C. The resulting slurry was cooled to 23° C. over 1 hour, cooled to 0-5° C. over 45 minutes and then stirred for 1 hour at 0-5° C. The slurry was filtered, washed with 18 mL 1:1 acetone:heptane, and dried under reduced pressure at room temperature to provide 4.25 g (77.8%) of the title compound.

EXAMPLE 21

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-α

A slurry of (N)-((S)-2-hydroxy-3-methyl-butyryl)-1-(L-alaninyl)-(S)-amino-3-methyl-2,3,4,5-tetrahydro-1H-3-benzazepin-2-one dihydrate (4.0 g.) and 3A ethanol (60 mL) was heated to 63-65° C. and stirred for 15 minutes. The mixture was cooled to 35° C. over 1 hour, seed crystals were added, and stirring continued at 35° C. for 2 hours. Heptane (60 mL) was added by syringe pump over 6 hours, maintaining the temperature at 35° C. The mixture was stirred an additional hour at 35° C., cooled to 23° C. over 6 hours and stirred for 2 hours. The slurry was filtered, washed with 12 mL 1:1 3A ethanol:heptane, and dried under reduced pressure at 40-45° C. for 20 hours to provide 2.6 g (67.7%) of the title compound.

EXAMPLE 22

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-α

(N)-((S)-2-hydroxy-3-methyl-butyryl)-1-(L-alaninyl)-(S)-amino-3-methyl-2,3,4,5-tetrahydro-1H-3-benzazepin-2-one dihydrate (1.3 kg) was placed in a Humidity Cabinet at 47% relative humidity at 70° C. for 45.5 hours to provide 1.2 k (92%) of the title compound.

EXAMPLE 23

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-α

(N)-((S)-2-hydroxy-3-methyl-butyryl)-1-(L-alaninyl)-(S)-amino-3-methyl-2,3,4,5-tetrahydro-1H-3-benzazepin-2-one dihydrate (2.4 kg) was placed in a 200 mm diameter, jacketed, agitated filter fitted with a porous metal filter media (~10 micron pore size) on the bottom of the filter, giving a bed depth of ~115 mm. The jacket of the agitated filter was maintained at a constant temperature of 20° C. Nitrogen was passed at a flow rate of 0.14 Kg/min through a vessel filled with acetone maintained at 5-6° C. and the resulting acetone-saturated nitrogen stream was heated to 20° C. by passing through a heat exchanger and then passed down-flow through the bed of dihydrate crystals in the agitated filter. Once each hour, the agitator blade was lowered into the solids, and agitated for 5 minutes to ensure uniformity. After 12 hours, the anhydrate Form-α crystals were discharged. Yield=100% of theory.

EXAMPLE 24

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-β

A mixture of 50 mg (N)-((S)-2-Hydroxy-3-methyl-butyryl)-1-(L-alaninyl)-(S)-amino-3-methyl-2,3,4,5-tetrahydro-1H-3-benzazepin-2-one dihydrate and 1 mL acetone was heated to a complete solution in a 2 mL glass vial. The solution was allowed to stand at room temperature overnight to provide the title compound as large needles. m.p.=217° C. (DSC, crimped aluminum pan heated from 25-300° C. at 10° C./minute).

EXAMPLE 25

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-β

A mixture of 261 mg (N)-((S)-2-Hydroxy-3-methyl-butyryl)-1-(L-alaninyl)-(S)-amino-3-methyl-2,3,4,5-tetrahydro-1H-3-benzazepin-2-one dihydrate and 5 mL acetone was heated to a complete solution. After slight cooling, seed crystals were added. The thick slurry was cooled to ambient temperature and then filtered to provide the title compound.

EXAMPLE 26

Synthesis of Crystalline (N)-((S)-2-hydroxy-3-methyl-butyryl)-1-(L-alaninyl)-(S)-amino-3-methyl-2,3,4,5-tetrahydro-1H-3-benzazepin-2-one anhydrate Form-β

A slurry of (N)-((S)-2-hydroxy-3-methyl-butyryl)-1-(L-alaninyl)-(S)-amino-3-methyl-2,3,4,5-tetrahydro-1H-3-benzazepin-2-one dihydrate (15.0 g.) and 3A ethanol (120 mL) was heated to 60° C., stirred for 15 minutes, and cooled to 45° C. over 30 minutes. Seed crystals (750 mg) were added and the mixture stirred at 45° C. for 2 hours. The slurry was cooled to 23° C. over 6 hours and stirred for 2 hours. The slurry was filtered, washed with 45 mL 3A ethanol, and dried under reduced pressure at 60° C. for 24 hours to provide 7.92 g (55%) of the title compound.

EXAMPLE 27

Synthesis of Amorphous (N)-((S)-2-hydroxy-3-methyl-butyryl)-1-(L-alaninyl)-(S)-amino-3-methyl-2,3,4,5-tetrahydro-1H-3-benzazepin-2-one anhydrate (N)-((S)-2-Hydroxy-3-methyl-butyryl)-1-(L-alaninyl)-(S)-amino-3-methyl-2,3,4,5-tetrahydro-1H-3-benzazepin-2-one dihydrate (97.15 g) was dried at 40° C. under vacuum for 38 hours to a weight loss of 8.8% to provide the title compound.

EXAMPLE 28

Synthesis of Amorphous (N)-((S)-2-hydroxy-3-methyl-butyryl)-1-(L-alaninyl)-(S)-amino-3-methyl-2,3,4,5-tetrahydro-1H-3-benzazepin-2-one anhydrate (N)-((S)-2-Hydroxy-3-methyl-butyryl)-1-(L-alaninyl)-(S)-amino-3-methyl-2,3,4,5-tetrahydro-1H-3-benzazepin-2-one dihydrate (7.0 g) was dried at 70° C. under vacuum for 24 hours to provide 6.4 g (91%) of the title compound.

When employed as a pharmaceutical the present invention is usually administered in the form of a pharmaceutical composition. Thus, in another embodiment, the present invention provides pharmaceutical compositions comprising an effective amount of N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate and a pharmaceutically acceptable diluent. Such compositions are used for inhibiting β-amyloid peptide release and/or its synthesis, including the treatment of Alzheimer' disease.

N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate can be administered by a variety of routes. The present compound can be administered in any form or mode which makes the compound bioavailable in an effective amount, including oral and parenteral routes. For example, N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate can be administered orally, by inhalation, subcutaneously, intramuscularly, intravenously, transdermally, intranasally, rectally, occularly, topically, sublingually, buccally, and the like.

In making the compositions of this invention, the active ingredient is usually mixed with an excipient, diluted by an excipient or enclosed within such a carrier which can be in the form of a capsule, sachet, paper or other container. N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate can be administered alone or in the form of a pharmaceutical composition, that is, combined with pharmaceutically acceptable diluents, such as carriers or excipients, the proportion and nature of which are determined by the solubility and chemical properties of the present compound, the chosen route of administration, and standard pharmaceutical practice. (*Remington's Pharmaceutical Sciences,* 18th Edition, Mack Publishing Co. (1990)).

The present pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 2% to about 90% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrants such as alginic acid, Primogel, corn starch and the like; lubricants such as magnesium stearate, silicon oil, or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral administration, N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate may be incorporated into a solution or suspension. These preparations typically contain at least 0.1% of a compound of the invention, but may be varied to be between 0.1 and about 90% of the weight thereof. The amount of the compound present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I or its pharmaceutical salt from about 0.1 to about 10% w/v (weight per unit volume).

Another preferred formulation of the present invention employs transdermal delivery devices ("patches"). Such transdermal patches may be used to provide continuous or discontinuous infusion of the compound of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

In order to more fully illustrate the operation of this invention, typical pharmaceutical compositions are described below. The examples are illustrative only, and are not intended to limit the scope of the invention in any way.

Formulation Example 1

Hard gelatin capsules containing the following ingredients are prepared:

| Ingredient | Quantity(mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity(mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity(mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |

-continued

| Ingredient | Quantity(mg/tablet) |
|---|---|
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity(mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) | |

-continued

| Ingredient | Amount |
|---|---|
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament are made as follows:

| Ingredient | Quantity(mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 560 mg quantities.

Formulation Example 9

A subcutaneous formulation may be prepared as follows:

| Ingredient | Quantity |
|---|---|
| Active Ingredient | 1.0 mg |
| corn oil | 1 ml |

Depending on the solubility of the active ingredient in corn oil, up to about 5.0 mg or more of the active ingredient may be employed in this formulation, if desired).

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

A tablet formulation may be prepared as follows:

| Ingredient | Quantity (mg/unit dose) |
|---|---|
| Inner Core | |
| N-(S)-2-hydroxy-3-methyl-butyryl)-1-(L-alaninyl)-(S)-1-amino-3-methyl-2,3,4,5-tetrahydro-1H-3-benzazepin-2-one dihydrate | 108.93 |
| Lactose monohydrate | 78.61 |
| Microcrystalline cellulose | 26.20 |
| Cross Povidone | 6.00 |
| Povidone | 9.00 |
| Coating | |
| Microcrystalline cellulose | 60.00 |
| Cross povidone | 9.00 |
| Magnesium stearate vegetable | 2.25 |
| TOTAL: | 300.00 |

The relative quantity of Lactose and Microcrystalline cellulose powders would be adjusted proportionately for higher and lower doses of the active ingredient to keep a total tablet weight of about 300 mg.

Formulation Example 12

A tablet formulation may be prepared as follows:

| Ingredient | Quantity (mg/unit dose) |
|---|---|
| Inner Core | |
| N-(S)-2-hydroxy-3-methyl-butyryl)-1-(L-alaninyl)-(S)-1-amino-3-methyl-2,3,4,5-tetrahydro-1H-3-benzazepin-2-one anhydrate | 100.00 |
| Lactose monohydrate | 85.31 |
| Microcrystalline cellulose | 28.44 |
| Cross Posvidone | 6.00 |
| Povidone | 9.00 |
| Coating | |
| Microcrystalline cellulose | 60.00 |
| Cross povidone | 9.00 |
| Magnesium stearate vegetable | 2.25 |
| TOTAL: | 300.00 |

The relative quantity of Lactose and Microcrystalline cellulose powders would be adjusted proportionately for higher and lower doses of the active ingredient to keep a total tablet weight of about 300 mg.

In one of its method aspects, this invention is directed to a method for inhibiting β-amyloid peptide release and/or its synthesis comprising administering to a patient in need thereof with an effective amount of N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-0, or crystalline N-(S)-2-hydroxy-3-methyl-butyryl)-1-(L-alaninyl)-

(S)-1-amino-3-methyl-2,3,4,5-tetrahydro-1H-3-benzazepin-2-one dihydrate. In a particular method embodiment, the present invention provides a method for treating Alzheimer's disease comprising administering to a patient in need thereof with an effective amount of N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate.

It is also recognized that-one skilled in the art may affect the Alzheimer's disease by treating a patient presently afflicted with the disease or by prophylactically treating a patient at risk to develop the disease. Thus, the terms "treatment" and "treating" are intended to refer to all processes wherein there may be a slowing, interrupting, arresting, controlling, or stopping of the progression of Alzheimer's disease, but does not necessarily indicate a total elimination of all symptoms. As such, the present methods include for preventing the onset of Alzheimer's disease in a patient at risk for developing Alzheimer's disease, inhibiting the progression of Alzheimer's disease, and treatment of advanced Alzheimer's disease.

As used herein, the term "patient" refers to a warm blooded animal, such as a mammal, which is afflicted with a disorder associated with increase β-amyloid peptide release and/or its synthesis, including Alzheimer's disease. It is understood that guinea pigs, dogs, cats, rats, mice, horses, cattle, sheep, and humans are examples of animals within the scope of the meaning of the term. Patients in need of such treatment are readily diagnosed.

As used herein, the term "effective amount" of a compound of formula I refers to an amount which is effective in inhibiting β-amyloid peptide release and/or its synthesis, and specifically, in treating Alzheimer's disease.

An effective amount can be readily determined by the attending diagnostician, as one skilled in the art, by the use of conventional techniques and by observing results obtained under analogous circumstances. In determining an effective amount, the dose of N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate, a number of factors are considered by the attending diagnostician, including, but not limited to: the potency and characteristics of N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate; the species of patient; its size, age, and general health; the degree of involvement or the severity of the disease; the response of the individual patient; the mode of administration; the bioavailability characteristics of the preparation administered; the dose regimen selected; the use of other concomitant medication; and other relevant circumstances.

An effective amount of N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate is expected to vary from about 0.1 milligram per kilogram of body weight per day (mg/kg/day) to about 100 mg/kg/day. Anticipated dosages are in the range of 50 to 200 mg/patient/day. Preferred dosages are in the range of 90 to 150 mg/patient/day. Most preferred dosages are in the range of 100 to 140 mg/patient/day. Further preferred amounts are able to be determined by one skilled in the art.

The N-(S)-2-hydroxy-3-methyl-butyryl)-1-(L-alaninyl)-(S)-1-amino-3-methyl-2,3,4,5-tetrahydro-1H-3-benzazepin-2-one, N-(S)-2-hydroxy-3-methyl-butyryl)-1-(L-alaninyl)-(S)-1-amino-3-methyl-2,3,4,5-tetrahydro-1H-3-benzazepin-2-one anhydrate, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-α, crystalline N-(S)-2-hydroxy-3-methyl-butyryl)-1-(L-alaninyl)-(S)-1-amino-3-methyl-2,3,4,5-tetrahydro-1H-3-benzazepin-2-one anhydrate Form-β, or crystalline N-(S)-2-hydroxy-3-methyl-butyryl)-1-(L-alaninyl)-(S)-1-amino-3-methyl-2,3,4,5-tetrahydro-1H-3-benzazepin-2-one dihydrate of the present invention can be tested in various biological systems including the following.

Example A

Cellular Screen for the Detection of Inhibitors of β-Amyloid Production

Numerous compounds of formula I above were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation $Lys_{651}Met_{652}$ to $Asn_{651}Leu_{652}$ (APP751 numbering) in the manner described in International Patent Application Publication No. 94/10569[8] and Citron et al.[12]. This mutation is commonly called the Swedish mutation and the cells, designated as "293 751 SWE", were plated in Corning 96-well plates at $2\text{-}4\times10^4$ cells per well in Dulbecco's minimal essential media (Sigma, St. Louis, Mo.) plus 10% fetal bovine serum. Cell number is important in order to achieve β-amyloid ELISA results within the linear range of the assay (~0.2 to 2.5 ng per 1 mL).

Following overnight incubation at 37° C. in an incubator equilibrated with 10% carbon dioxide, media were removed and replaced with 200 mL of a compound of formula I (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media. From each well, 100 μL of conditioned media or appropriate dilutions thereof were transferred into an ELISA plate precoated with antibody 266 [P. Seubert, *Nature* (1992) 359:325-327] against amino acids 13-28 of β-amyloid peptide as described in International Patent Application Publication No. 94/10569 and stored at 4° C. overnight. An ELISA assay employing labeled antibody 3D6 [P. Seubert, *Nature* (1992) 359:325-327] against amino acids 1-5 of β-amyloid peptide was run the next day to measure the amount of β-amyloid peptide produced.

Cytotoxic effects of the compounds were measured by a modification of the method of Hansen, et al. To the cells remaining in the tissue culture plate was added 25 μL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562}$ nm and the $OD_{650}$ nm was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

Example B

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) *Nature* 373: 523-527]. Depending upon which compound is being tested, the compound is usually formulated at between 1 and 10 mg/mL. Because of the low solubility factors of the compounds, they may be formulated with various vehicles, such as corn oil (Safeway, South San Francisco, Calif.); 10% ethanol in corn oil; 2-hydroxypropyl-1-cyclodextrin (Research Biochemicals International, Natick Mass); and carboxy-methyl-cellulose (Sigma Chemical Co., St. Louis Mo.).

The mice are dosed subcutaneously with a 26 gauge needle and 3 hours later the animals are euthanized via $CO_2$ narcosis and blood is taken by cardiac puncture using a 1 cc 25 G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/ml aprotinin, 5 mM EDTA, pH 8.0, 10 μg/ml leupeptin], thereby reducing the final concentration of guanidine to 0.5 M, before centrifugation at 16,000×g for 20 minutes at 4° C. Samples are further diluted, if necessary, to achieve an optimal range for the ELISA measurements by the addition of casein buffer with 0.5 M guanidine hydrochloride added. The β-amyloid standards (1-40 or 1-42 amino acids) were prepared such that the final composition equaled 0.5 M guanidine in the presence of 0.1% bovine serum albumin (BSA).

The total β-amyloid sandwich ELISA, quantitating both β-amyloid (aa 1-40) and β-amyloid (aa 1-42) consists of two monoclonal antibodies (mAb) to β-amyloid. The capture antibody, 266 [P. Seubert, *Nature* (1992) 359:325-327], is specific to amino acids 13-28 of β-amyloid. The antibody 3D6 [Johnson-Wood et al., *PNAS USA* (1997) 94:1550-1555], which is specific to amino acids 1-5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/ml (11 pM) and shows no cross-reactivity to the endogenous murine β-amyloid peptide at concentrations up to 1 ng/ml.

The configuration of the sandwich ELISA quantitating the level of β-amyloid (aa 1-42) employs the mAb 21F12 [Johnson-Wood et al., *PNAS USA* (1997) 94:1550-1555] (which recognizes amino acids 33-42 of β-amyloid) as the capture antibody. Biotinylated 3D6 is also the reporter antibody in this assay which has a lower limit of sensitivity of ~125 pg/ml (28 pM).

The 266 and 21F12 capture mAbs are coated at 10 μg/ml into 96 well immunoassay plates (Costar, Cambridge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed 3 times with wash buffer between each step of the assay. The biotinylated 3D6, diluted to 0.5 μg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colormetric substrate, Slow TMB-ELISA (Pierce, Cambridge Mass.), is added and allowed to react for 15 minutes, after which the enzymatic reaction is stopped with addition of 2 $NH_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5 gm/l thimerosal, 8.5 gm/l sodium chloride, 0.5 ml Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

From the foregoing description, various modifications and changes in the composition and method will occur to those skilled in the art. All such modifications coming within the scope of the appended claims are intended to be included therein.

We claim:

1. (N)-((S)-2-Hydroxy-3-methyl-butyryl)-1-(L-alaninyl)-(S)-1-amino-3-methyl-2,3,4,5-tetrahydro-1H-3-benzazepin-2-one or the dihydrate thereof.

2. The compound of claim 1 as the anhydrate.

3. The compound of claim 2 as the crystalline anhydrate Form-α characterized by at least one of the following:
   a) an X-ray powder diffraction pattern comprising a peak at 4.53, 5.36, 9.52, 9.79, 11.69, 12.46, 13.91, 14.72, 16.21, 17.92, or 19.10 (2θ±0.2°);
   b) an X-ray powder diffraction pattern comprising peaks at 9.52 and 9.79 (2θ±0.2°); 4.53 and 9.52 (2θ±0.2°); 4.53 and 9.79 (2θ±0.2°); or 9.52, 9.79, and 12.46 (2θ±0.2°);
   c) a solid state $^{13}C$ nuclear magnetic resonance spectrum having a peak at chemical shift 78.0, 79.0, 122.9, 135.5, 168.6, 169.5, or 177.8±0.1 ppm; and
   d) a DSC melting point of 214° C.

4. The compound of claim 2 as the crystalline anhydrate Form-β characterized by at least one of the following:
   a) an X-ray powder diffraction pattern comprising a peak at 8.10, or 10.66 (2θ±0.2°);
   b) a solid state $^{13}C$ nuclear magnetic resonance spectrum having a peak at chemical shift 19.1, 77.2, or 130.5+/−0.1 ppm; and
   c) a DSC melting point of 217° C.

5. The compound of claim 1 as the dihydrate in the crystalline form characterized by at least one of the following:
   a) an X-ray powder diffraction pattern comprising a peak at 8.36, 12.43, 15.34, 19.22, 20.50, or 20.63 (2θ±0.2°);
   b) an X-ray powder diffraction pattern comprising peaks at 8.36 and 15.34 (2θ±0.2°); 8.36 and 12.43 (2θ±0.2°); 8.36, 12.43, and 15.34 (2θ±0.2°);
   c) a solid state $^{13}C$ nuclear magnetic resonance spectrum having a peak at chemical shift 75.6, 35.3, 21.4, or 16.6±0.5 ppm.

6. A pharmaceutical composition comprising (N)-((S)-2-hydroxy-3-methyl-butyryl)-1-(L-alaninyl)-(S)-1-amino-3-methyl-2,3,4,5-tetrahydro-1H-3-benzazepin-2-one or the dihydrate thereof and a pharmaceutically acceptable diluent.

7. A pharmaceutical composition of claim 6 comprising (N)-((S)-2-hydroxy-3-methyl-butyryl)-1-(L-alaninyl)-(S)-1-amino-3-methyl-2,3,4,5-tetrahydro-1H-3-benzazepin-2-one anhydrate.

8. A pharmaceutical composition of claim 7 wherein (N)-((S)-2-hydroxy-3-methyl-butyryl)-1-(L-alaninyl)-(S)-1-amino-3-methyl-2,3,4,5-tetrahydro-1H-3-benzazepin-2-one is in crystalline anhydrate Form-α.

9. A pharmaceutical composition of claim 7 wherein (N)-((S)-2-hydroxy-3-methyl-butyryl)-1-(L-alaninyl)-(S)-1-amino-3-methyl-2,3,4,5-tetrahydro-1H-3-benzazepin-2-one is in crystalline anhydrate Form-β.

10. A pharmaceutical composition of claim 6 comprising (N)-((S)-2-hydroxy-3-methyl-butyryl)-1-(L-alaninyl)-(S)-1-amino-3-methyl-2,3,4,5-tetrahydro-1H-3-benzazepin-2-one dihydrate and a pharmaceutically acceptable diluent.

11. A method of treating Alzheimer's disease comprising administering to a patient in need thereof with an effective amount of (N)-((S)-2-hydroxy-3-methyl-butyryl)-1-(L-alaninyl)-(S)-1-amino-3-methyl-2,3,4,5-tetrahydro-1H-3-benzazepin-2-one or the dihydrate thereof.

12. A method of claim 11 comprising administering (N)-((S)-2-hydroxy-3-methyl-butyryl)-1-(L-alaninyl)-(S)-1-amino-3-methyl-2,3,4,5-tetrahydro-1H-3-benzazepin-2-one anhydrate.

13. A method of claim 12 wherein (N)-((S)-2-hydroxy-3-methyl-butyryl)-1-(L-alaninyl)-(S)-1-amino-3-methyl-2,3,4,5-tetrahydro-1H-3-benzazepin-2-one anhydrate is in crystalline Form-α.

14. A method of claim 12 wherein (N)-((S)-2-hydroxy-3-methyl-butyryl)-1-(L-alaninyl)-(S)-1-amino-3-methyl-2,3,4,5-tetrahydro-1H-3-benzazepin-2-one anhydrate is in crystalline Form-β.

15. A method of claim 11 comprising administering (N)-((S)-2-hydroxy-3-methyl-butyryl)-1-(L-alaninyl)-(S)-1-amino-3-methyl-2,3,4,5-tetrahydro-1H-3-benzazepin-2-one dihydrate.

* * * * *